United States Patent
Chen et al.

(10) Patent No.: US 12,380,981 B2
(45) Date of Patent: Aug. 5, 2025

(54) CLOSED LOOP CONTROL OF PHYSIOLOGICAL GLUCOSE

(71) Applicant: Ypsomed AG, Burgdorf (CH)

(72) Inventors: Yamei Chen, Carmel, IN (US); Haoda Fu, Carmel, IN (US); Parag Garhyan, Carmel, IN (US); Ahmad Haidar, Montreal (CA); Richard Earl Jones, Jr., Plainfield, IN (US); Christopher Kovalchick, Bedford, MA (US); Marie Kearney Schiller, Wellesley, MA (US); Monica Rixman Swinney, Stoneham, MA (US); Howard Allan Wolpert, Brookline, MA (US)

(73) Assignee: Ypsomed AG, Burgdorf (CH)

( * ) Notice: Subject to any disclaimer, the term of this patent is extended or adjusted under 35 U.S.C. 154(b) by 0 days.

(21) Appl. No.: 18/404,380

(22) Filed: Jan. 4, 2024

(65) Prior Publication Data
US 2024/0161900 A1    May 16, 2024

(51) Int. Cl.
| G16H 20/17 | (2018.01) |
| A61M 5/172 | (2006.01) |
| G16H 50/50 | (2018.01) |

(52) U.S. Cl.
CPC .......... *G16H 20/17* (2018.01); *A61M 5/1723* (2013.01); *G16H 50/50* (2018.01)

(58) Field of Classification Search
CPC ...... G16H 50/50; G16H 20/17; A61M 5/1723
See application file for complete search history.

(56) References Cited

U.S. PATENT DOCUMENTS

| 4,475,901 A | 10/1984 | Kraegen et al. |
| 5,822,715 A | 10/1998 | Worthington et al. |
| 5,853,364 A | 12/1998 | Baker et al. |
| 5,938,594 A | 8/1999 | Poon et al. |
| 5,971,922 A | 10/1999 | Arita et al. |
| 6,083,172 A | 7/2000 | Baker et al. |
| 6,175,752 B1 | 1/2001 | Say et al. |
| 6,269,314 B1 | 7/2001 | Iitawaki et al. |
| 6,459,939 B1 | 10/2002 | Hugo |
| 6,544,212 B2 | 4/2003 | Galley et al. |
| 6,558,351 B1 | 5/2003 | Steil et al. |
| 6,572,545 B2 | 6/2003 | Knobbe et al. |
| 6,575,905 B2 | 6/2003 | Knobbe et al. |
| 6,691,043 B2 | 2/2004 | Ribeiro |
| 6,740,072 B2 | 5/2004 | Starkweather et al. |
| 6,827,702 B2 | 12/2004 | Lebel et al. |

(Continued)

FOREIGN PATENT DOCUMENTS

| CN | 104667379 A | 6/2015 |
| EP | 3053279 B1 | 4/2021 |

(Continued)

OTHER PUBLICATIONS

Resalat et al, Design of a Dual-Hormone Model Predictive Control for Artificial Pancreas with Exercise Model, Conf Proc IEEE Eng Med Biol Soc. 2016 2270-2273 (Aug. 2016) (Year: 2016).*

(Continued)

*Primary Examiner* — Jordan L Jackson
(74) *Attorney, Agent, or Firm* — Dorsey & Whitney LLP

(57) ABSTRACT

The present disclosure relates to systems and methods for controlling physiological glucose concentrations in a patient.

12 Claims, 11 Drawing Sheets

(56) References Cited

U.S. PATENT DOCUMENTS

| | | |
|---|---|---|
| 6,923,763 B1 | 8/2005 | Kovatchev et al. |
| 7,022,072 B2 | 4/2006 | Fox et al. |
| 7,025,743 B2 | 4/2006 | Mann et al. |
| 7,060,059 B2 | 6/2006 | Keith et al. |
| 7,267,665 B2 | 9/2007 | Steil et al. |
| 7,278,983 B2 | 10/2007 | Ireland et al. |
| 7,287,487 B2 | 10/2007 | Hurwitz |
| 7,354,420 B2 | 4/2008 | Steil et al. |
| 7,395,216 B2 | 7/2008 | Rosenfeld et al. |
| 7,399,277 B2 | 7/2008 | Saidara et al. |
| 7,402,153 B2 | 7/2008 | Steil et al. |
| 7,491,187 B2 | 2/2009 | Van et al. |
| 7,547,261 B2 | 6/2009 | Morrow et al. |
| 7,569,030 B2 | 8/2009 | Lebel et al. |
| 7,590,443 B2 | 9/2009 | Bharmi |
| 7,651,845 B2 | 1/2010 | Doyle et al. |
| 7,704,226 B2 | 4/2010 | Mueller et al. |
| 7,727,147 B1 | 6/2010 | Osorio et al. |
| 7,766,830 B2 | 8/2010 | Fox et al. |
| 7,766,831 B2 | 8/2010 | Essenpreis et al. |
| 7,778,680 B2 | 8/2010 | Goode et al. |
| 7,785,313 B2 | 8/2010 | Mastrototaro |
| 7,806,854 B2 | 10/2010 | Damiano et al. |
| 7,806,886 B2 | 10/2010 | Kanderian et al. |
| 7,819,843 B2 | 10/2010 | Mann et al. |
| 7,850,641 B2 | 12/2010 | Lebel et al. |
| 7,860,544 B2 | 12/2010 | Say et al. |
| 7,879,026 B2 | 2/2011 | Estes et al. |
| 7,890,295 B2 | 2/2011 | Shin et al. |
| 7,899,545 B2 | 3/2011 | John |
| 7,901,394 B2 | 3/2011 | Ireland et al. |
| 7,912,684 B2 | 3/2011 | Brown |
| 7,920,998 B2 | 4/2011 | Brown |
| 7,925,321 B2 | 4/2011 | Goode et al. |
| 7,937,255 B2 | 5/2011 | Brown |
| 7,941,200 B2 | 5/2011 | Weinert et al. |
| 7,959,569 B2 | 6/2011 | Goode et al. |
| 7,963,917 B2 | 6/2011 | Kellogg et al. |
| 8,062,249 B2 | 11/2011 | Wilinska et al. |
| 8,088,098 B2 | 1/2012 | Yodfat et al. |
| 8,105,268 B2 | 1/2012 | Lebel et al. |
| 8,109,921 B2 | 2/2012 | Estes et al. |
| 8,112,375 B2 | 2/2012 | Pav |
| 8,114,023 B2 | 2/2012 | Ward et al. |
| 8,140,312 B2 | 3/2012 | Hayter et al. |
| 8,152,789 B2 | 4/2012 | Starkweather et al. |
| 8,162,829 B2 | 4/2012 | Say et al. |
| 8,177,716 B2 | 5/2012 | Say et al. |
| 8,192,395 B2 | 6/2012 | Estes et al. |
| 8,208,984 B2 | 6/2012 | Blomquist et al. |
| 8,226,556 B2 | 7/2012 | Hayes et al. |
| 8,229,872 B2 | 7/2012 | Gilhuly |
| 8,257,300 B2 | 9/2012 | Budiman et al. |
| 8,273,052 B2 | 9/2012 | Damiano et al. |
| 8,290,562 B2 | 10/2012 | Goode et al. |
| 8,318,154 B2 | 11/2012 | Frost et al. |
| 8,346,399 B2 | 1/2013 | Blomquist |
| 8,348,886 B2 | 1/2013 | Kanderian et al. |
| 8,348,923 B2 | 1/2013 | Kanderian et al. |
| 8,377,031 B2 | 2/2013 | Hayter et al. |
| 8,398,616 B2 | 3/2013 | Budiman |
| 8,409,131 B2 | 4/2013 | Say et al. |
| 8,414,523 B2 | 4/2013 | Blomquist et al. |
| 8,449,524 B2 | 5/2013 | Braig et al. |
| 8,460,231 B2 | 6/2013 | Brauker et al. |
| 8,467,972 B2 | 6/2013 | Rush |
| 8,478,557 B2 | 7/2013 | Hayter et al. |
| 8,480,580 B2 | 7/2013 | Wolpert et al. |
| 8,480,649 B2 | 7/2013 | Yodfat et al. |
| 8,504,179 B2 | 8/2013 | Blomquist |
| 8,527,208 B2 | 9/2013 | Prud et al. |
| 8,532,933 B2 | 9/2013 | Duke et al. |
| 8,548,544 B2 | 10/2013 | Kircher et al. |
| 8,560,082 B2 | 10/2013 | Wei |
| 8,562,587 B2 | 10/2013 | Kovatchev et al. |
| 8,579,854 B2 | 11/2013 | Budiman et al. |
| 8,585,591 B2 | 11/2013 | Sloan et al. |
| 8,585,593 B2 | 11/2013 | Kovatchev et al. |
| 8,585,637 B2 | 11/2013 | Wilinska et al. |
| 8,597,274 B2 | 12/2013 | Sloan et al. |
| 8,615,366 B2 | 12/2013 | Galley et al. |
| 8,622,988 B2 | 1/2014 | Hayter |
| 8,647,321 B2 | 2/2014 | Budiman |
| 8,657,807 B2 | 2/2014 | Blomquist |
| 8,660,800 B2 | 2/2014 | Von Busch et al. |
| 8,688,386 B2 | 4/2014 | Shadforth et al. |
| 8,690,820 B2 | 4/2014 | Cinar et al. |
| 8,690,856 B2 | 4/2014 | Blomquist |
| 8,718,943 B2 | 5/2014 | Moerman |
| 8,718,965 B2 | 5/2014 | Hayter et al. |
| 8,732,188 B2 | 5/2014 | Doniger et al. |
| 8,734,422 B2 | 5/2014 | Hayter |
| 8,734,428 B2 | 5/2014 | Blomquist |
| 8,744,545 B2 | 6/2014 | Say et al. |
| 8,753,316 B2 | 6/2014 | Blomquist |
| 8,756,043 B2 | 6/2014 | Albisser et al. |
| 8,762,070 B2 | 6/2014 | Doyle, III et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,784,369 B2 | 7/2014 | Starkweather et al. |
| 8,784,370 B2 | 7/2014 | Lebel et al. |
| 8,788,044 B2 | 7/2014 | John |
| 8,795,224 B2 | 8/2014 | Starkweather et al. |
| 8,795,252 B2 | 8/2014 | Hayter |
| 8,821,433 B2 | 9/2014 | Blomquist |
| 8,823,528 B2 | 9/2014 | Blomquist |
| 8,825,166 B2 | 9/2014 | John |
| 8,831,735 B2 | 9/2014 | John |
| 8,840,553 B2 | 9/2014 | Say et al. |
| 8,840,582 B2 | 9/2014 | Blomquist et al. |
| 8,876,755 B2 | 11/2014 | Taub et al. |
| 8,876,803 B2 | 11/2014 | Budiman |
| 8,924,160 B2 | 12/2014 | Moerman |
| 8,924,161 B2 | 12/2014 | Moerman |
| 8,926,585 B2 | 1/2015 | Brauker et al. |
| 8,930,203 B2 | 1/2015 | Kiaie et al. |
| 8,932,216 B2 | 1/2015 | Jennewine |
| 8,936,573 B2 | 1/2015 | Blomquist |
| 8,945,094 B2 | 2/2015 | Nordh |
| 8,954,373 B2 | 2/2015 | Atlas et al. |
| 8,961,416 B2 | 2/2015 | Siddiqui et al. |
| 8,961,465 B2 | 2/2015 | Blomquist |
| 8,965,509 B2 | 2/2015 | John |
| 8,974,439 B2 | 3/2015 | Estes |
| 8,977,504 B2 | 3/2015 | Hovorka |
| 8,998,878 B2 | 4/2015 | Blomquist |
| 9,017,311 B2 | 4/2015 | Budiman |
| 9,037,254 B2 | 5/2015 | John |
| 9,056,167 B2 | 6/2015 | Pesach et al. |
| 9,056,168 B2 | 6/2015 | Kircher, Jr. et al. |
| 9,066,694 B2 | 6/2015 | Say et al. |
| 9,089,292 B2 | 7/2015 | Roy et al. |
| 9,089,713 B2 | 7/2015 | John |
| 9,114,210 B2 | 8/2015 | Estes |
| 9,119,528 B2 | 9/2015 | Cobelli et al. |
| 9,192,750 B2 | 11/2015 | Pettis et al. |
| 9,199,031 B2 | 12/2015 | Yodfat et al. |
| 9,220,456 B2 | 12/2015 | Bashan et al. |
| 9,227,014 B2 | 1/2016 | Buckingham et al. |
| 9,244,077 B2 | 1/2016 | Yodfat et al. |
| 9,254,362 B2 | 2/2016 | Estes et al. |
| 9,283,323 B2 | 3/2016 | Toumazou et al. |
| 9,302,045 B2 | 4/2016 | Rule |
| 9,320,471 B2 | 4/2016 | Hayes et al. |
| 9,323,898 B2 | 4/2016 | Sloan et al. |
| 9,330,237 B2 | 5/2016 | Cohen et al. |
| 9,333,298 B2 | 5/2016 | Kim et al. |
| 9,364,609 B2 | 6/2016 | Keenan et al. |
| 9,364,679 B2 | 6/2016 | John |
| 9,398,869 B2 | 7/2016 | Kovatchev et al. |
| 9,399,096 B2 | 7/2016 | Keenan et al. |
| 9,402,953 B2 | 8/2016 | Wilinska et al. |
| 9,420,968 B2 | 8/2016 | Kamath et al. |

(56) References Cited

U.S. PATENT DOCUMENTS

| | | |
|---|---|---|
| 9,440,025 B2 | 9/2016 | Kanderian, Jr. et al. |
| 9,445,757 B2 | 9/2016 | Desborough et al. |
| 9,457,145 B2 | 10/2016 | Yodfat et al. |
| 9,474,855 B2 | 10/2016 | Mccann et al. |
| 9,480,796 B2 | 11/2016 | Starkweather et al. |
| 9,483,619 B2 | 11/2016 | Fischell et al. |
| 9,486,171 B2 | 11/2016 | Saint |
| 9,486,578 B2 | 11/2016 | Finan et al. |
| 9,507,917 B2 | 11/2016 | Atlas et al. |
| 9,510,782 B2 | 12/2016 | Kamath et al. |
| 9,517,306 B2 | 12/2016 | Morales |
| 9,526,834 B2 | 12/2016 | Keenan et al. |
| 9,572,934 B2 | 2/2017 | Hayter |
| 9,579,456 B2 | 2/2017 | Budiman et al. |
| 9,597,451 B2 | 3/2017 | Yodfat et al. |
| 9,610,046 B2 | 4/2017 | Hayter |
| 9,619,625 B2 | 4/2017 | Bengtsson |
| 9,623,179 B2 | 4/2017 | Mastrototaro et al. |
| 9,629,957 B2 | 4/2017 | Sigrist et al. |
| 9,636,461 B2 | 5/2017 | Bengtsson et al. |
| 9,649,439 B2 | 5/2017 | John |
| 9,662,445 B2 | 5/2017 | Parikh et al. |
| 9,669,160 B2 | 6/2017 | Harris et al. |
| 9,669,162 B2 | 6/2017 | Sloan et al. |
| 9,687,194 B2 | 6/2017 | Cantwell et al. |
| 9,693,700 B2 | 7/2017 | Tan et al. |
| 9,694,133 B2 | 7/2017 | Kircher, Jr. et al. |
| 9,700,708 B2 | 7/2017 | Doyle, III et al. |
| 9,717,848 B2 | 8/2017 | Geismar et al. |
| 9,724,470 B2 | 8/2017 | Day et al. |
| 9,750,438 B2 | 9/2017 | Kovatchev et al. |
| 9,757,510 B2 | 9/2017 | Finan |
| 9,782,540 B2 | 10/2017 | Lebel et al. |
| 9,795,737 B2 | 10/2017 | Finan et al. |
| 9,808,577 B2 | 11/2017 | Nagar et al. |
| 9,833,177 B2 | 12/2017 | Blomquist |
| 9,833,191 B2 | 12/2017 | Mazlish |
| 9,833,570 B2 | 12/2017 | El-khatib et al. |
| 9,833,571 B2 | 12/2017 | Budiman |
| 9,844,627 B2 | 12/2017 | Estes |
| 9,848,774 B2 | 12/2017 | Bergstrom et al. |
| 9,849,239 B2 | 12/2017 | Grosman et al. |
| 9,861,310 B2 | 1/2018 | O'connell |
| 9,861,747 B2 | 1/2018 | Chovanda et al. |
| 9,861,748 B2 | 1/2018 | Mastrototaro et al. |
| 9,872,890 B2 | 1/2018 | Davidson et al. |
| 9,878,096 B2 | 1/2018 | Roy et al. |
| 9,878,097 B2 | 1/2018 | Estes |
| 9,886,556 B2 | 2/2018 | Booth et al. |
| 9,889,250 B2 | 2/2018 | Blomquist et al. |
| 9,907,515 B2 | 3/2018 | Doyle, III et al. |
| 9,907,909 B2 | 3/2018 | Finan et al. |
| 9,913,599 B2 | 3/2018 | Bernstein et al. |
| 9,918,635 B2 | 3/2018 | Bousamra et al. |
| 9,919,105 B2 | 3/2018 | Yodfat et al. |
| 9,936,910 B2 | 4/2018 | Hayter et al. |
| 9,943,644 B2 | 4/2018 | Hayter |
| 9,943,645 B2 | 4/2018 | Monirabbasi et al. |
| 9,965,596 B2 | 5/2018 | Booth et al. |
| 9,984,773 B2 | 5/2018 | Gondhalekar et al. |
| 9,990,581 B2 | 6/2018 | Carlsgaard et al. |
| 9,999,728 B2 | 6/2018 | Parikh et al. |
| 10,007,765 B2 | 6/2018 | Nogueira et al. |
| 10,010,273 B2 | 7/2018 | Sloan et al. |
| 10,016,561 B2 | 7/2018 | Saint et al. |
| 10,022,498 B2 | 7/2018 | Ruchti et al. |
| 10,046,113 B2 | 8/2018 | Ruchti et al. |
| 10,052,049 B2 | 8/2018 | Blomquist et al. |
| 10,080,529 B2 | 9/2018 | Fox et al. |
| 10,130,765 B2 | 11/2018 | Budiman et al. |
| 2003/0187337 A1 | 10/2003 | Tarassenko et al. |
| 2003/0195404 A1 | 10/2003 | Knobbe et al. |
| 2004/0034295 A1 | 2/2004 | Salganicoff |
| 2004/0044272 A1 | 3/2004 | Moerman et al. |
| 2004/0248204 A1 | 12/2004 | Moerman |
| 2005/0004439 A1 | 1/2005 | Shin et al. |
| 2005/0075274 A1 | 4/2005 | Willmann et al. |
| 2005/0171503 A1 | 8/2005 | Van et al. |
| 2005/0197621 A1 | 9/2005 | Poulsen et al. |
| 2006/0253296 A1 | 11/2006 | Liisberg et al. |
| 2007/0016127 A1 | 1/2007 | Staib et al. |
| 2007/0088271 A1 | 4/2007 | Richards |
| 2008/0183060 A1 | 7/2008 | Steil et al. |
| 2008/0206799 A1 | 8/2008 | Blomquist |
| 2008/0228056 A1 | 9/2008 | Blomquist et al. |
| 2009/0163402 A1 | 6/2009 | George |
| 2009/0163781 A1 | 6/2009 | Say et al. |
| 2009/0227940 A1 | 9/2009 | Say et al. |
| 2009/0227941 A1 | 9/2009 | Say et al. |
| 2009/0318791 A1 | 12/2009 | Kaastrup |
| 2010/0049022 A1 | 2/2010 | Parris et al. |
| 2010/0057043 A1 | 3/2010 | Kovatchev et al. |
| 2010/0145262 A1 | 6/2010 | Bengtsson et al. |
| 2010/0160740 A1 | 6/2010 | Cohen et al. |
| 2010/0168543 A1 | 7/2010 | Kamath et al. |
| 2010/0168657 A1 | 7/2010 | Kamath et al. |
| 2010/0174228 A1 | 7/2010 | Buckingham et al. |
| 2010/0185073 A1 | 7/2010 | Goode et al. |
| 2010/0249561 A1 | 9/2010 | Patek et al. |
| 2010/0262117 A1 | 10/2010 | Magni et al. |
| 2010/0292553 A1 | 11/2010 | Say et al. |
| 2010/0298681 A1 | 11/2010 | Say et al. |
| 2011/0077481 A1 | 3/2011 | Say et al. |
| 2011/0098548 A1 | 4/2011 | Budiman et al. |
| 2011/0184267 A1 | 7/2011 | Duke et al. |
| 2011/0275410 A1 | 11/2011 | Caffey et al. |
| 2011/0313390 A1 | 12/2011 | Roy et al. |
| 2011/0313680 A1 | 12/2011 | Doyle et al. |
| 2012/0078067 A1 | 3/2012 | Kovatchev et al. |
| 2012/0238851 A1 | 9/2012 | Kamen et al. |
| 2012/0330228 A1 | 12/2012 | Day et al. |
| 2013/0041343 A1 | 2/2013 | Toumazou et al. |
| 2013/0085679 A1 | 4/2013 | Budiman |
| 2013/0190583 A1 | 7/2013 | Grosman et al. |
| 2013/0231543 A1 | 9/2013 | Facchinetti et al. |
| 2013/0231642 A1 | 9/2013 | Doyle et al. |
| 2013/0245547 A1 | 9/2013 | El-khatib et al. |
| 2013/0245663 A1 | 9/2013 | Voss et al. |
| 2013/0274576 A1 | 10/2013 | Amirouche et al. |
| 2013/0277287 A1 | 10/2013 | Moissl et al. |
| 2013/0345664 A1 | 12/2013 | Beck et al. |
| 2014/0005633 A1 | 1/2014 | Finan |
| 2014/0051957 A1 | 2/2014 | Say et al. |
| 2014/0066886 A1 | 3/2014 | Roy et al. |
| 2014/0066887 A1 | 3/2014 | Mastrototaro et al. |
| 2014/0066890 A1 | 3/2014 | Sloan et al. |
| 2014/0081236 A1 | 3/2014 | Wilinska et al. |
| 2014/0088393 A1 | 3/2014 | Bernstein et al. |
| 2014/0107607 A1 | 4/2014 | Estes |
| 2014/0121488 A1 | 5/2014 | Budiman |
| 2014/0163517 A1 | 6/2014 | Finan et al. |
| 2014/0180203 A1 | 6/2014 | Budiman et al. |
| 2014/0180240 A1 | 6/2014 | Finan et al. |
| 2014/0200559 A1 | 7/2014 | Doyle et al. |
| 2014/0221966 A1 | 8/2014 | Buckingham et al. |
| 2014/0235981 A1 | 8/2014 | Hayter |
| 2014/0276554 A1 | 9/2014 | Finan et al. |
| 2014/0303552 A1 | 10/2014 | Kanderian et al. |
| 2014/0309511 A1 | 10/2014 | Stål |
| 2014/0309615 A1 | 10/2014 | Mazlish |
| 2014/0323961 A1 | 10/2014 | Blomquist et al. |
| 2014/0324020 A1 | 10/2014 | Stefansen |
| 2014/0344289 A1 | 11/2014 | Berenson et al. |
| 2014/0371515 A1 | 12/2014 | John |
| 2014/0371682 A1 | 12/2014 | Bengtsson et al. |
| 2015/0018633 A1 | 1/2015 | Kovachev et al. |
| 2015/0025495 A1 | 1/2015 | Peyser |
| 2015/0045641 A1 | 2/2015 | Rule |
| 2015/0057606 A1 | 2/2015 | Taub et al. |
| 2015/0080756 A1 | 3/2015 | Robinson et al. |
| 2015/0100038 A1 | 4/2015 | Mccann et al. |
| 2015/0157273 A1 | 6/2015 | An et al. |
| 2015/0157793 A1 | 6/2015 | Kovelman |
| 2015/0157794 A1 | 6/2015 | Roy et al. |

(56) References Cited

U.S. PATENT DOCUMENTS

| | | |
|---|---|---|
| 2015/0157795 A1 | 6/2015 | Valk et al. |
| 2015/0164414 A1 | 6/2015 | Matthews |
| 2015/0165119 A1 | 6/2015 | Palerm et al. |
| 2015/0190098 A1 | 7/2015 | Patek et al. |
| 2015/0220702 A1 | 8/2015 | Hovorka |
| 2015/0282744 A1 | 10/2015 | Roy et al. |
| 2015/0289821 A1 | 10/2015 | Rack-gomer et al. |
| 2015/0306312 A1 | 10/2015 | Palerm |
| 2015/0306314 A1 | 10/2015 | Doyle et al. |
| 2015/0328403 A1 | 11/2015 | Dobbles et al. |
| 2015/0331418 A1 | 11/2015 | Nogueira et al. |
| 2015/0331419 A1 | 11/2015 | Nogueira et al. |
| 2015/0352282 A1 | 12/2015 | Mazlish |
| 2016/0000998 A1* | 1/2016 | Estes ............ A61M 5/24 604/892.1 |
| 2016/0007890 A1 | 1/2016 | Kovatchev et al. |
| 2016/0022180 A1 | 1/2016 | Joseph et al. |
| 2016/0029966 A1 | 2/2016 | Salas-boni et al. |
| 2016/0038673 A1 | 2/2016 | Morales |
| 2016/0073952 A1 | 3/2016 | Bashan et al. |
| 2016/0073964 A1 | 3/2016 | Cobelli et al. |
| 2016/0074582 A1 | 3/2016 | Becker |
| 2016/0113558 A1 | 4/2016 | Bhavaraju et al. |
| 2016/0162662 A1 | 6/2016 | Monirabbasi et al. |
| 2016/0162797 A1 | 6/2016 | Thorpe et al. |
| 2016/0174911 A1 | 6/2016 | Palerm et al. |
| 2016/0175520 A1 | 6/2016 | Palerm et al. |
| 2016/0193409 A1 | 7/2016 | Facchinetti et al. |
| 2016/0256087 A1 | 9/2016 | Doyle et al. |
| 2016/0256629 A1 | 9/2016 | Grosman et al. |
| 2016/0287184 A1 | 10/2016 | Diebold et al. |
| 2016/0317743 A1 | 11/2016 | Estes |
| 2016/0331310 A1 | 11/2016 | Kovatchev |
| 2016/0331898 A1 | 11/2016 | Damiano et al. |
| 2016/0354543 A1 | 12/2016 | Cinar et al. |
| 2017/0021100 A1 | 1/2017 | Starkweather et al. |
| 2017/0035969 A1 | 2/2017 | Sloan et al. |
| 2017/0049383 A1 | 2/2017 | Mcmahon et al. |
| 2017/0049386 A1 | 2/2017 | Abraham et al. |
| 2017/0053072 A1 | 2/2017 | Agrawal et al. |
| 2017/0053084 A1 | 2/2017 | Mcmahon et al. |
| 2017/0053552 A1 | 2/2017 | Zhong et al. |
| 2017/0065212 A1 | 3/2017 | Gottlieb et al. |
| 2017/0080152 A1 | 3/2017 | Wilinska et al. |
| 2017/0091419 A1 | 3/2017 | Hoglund et al. |
| 2017/0119968 A1 | 5/2017 | Keenan et al. |
| 2017/0135643 A1 | 5/2017 | Budiman et al. |
| 2017/0143899 A1 | 5/2017 | Gondhalekar et al. |
| 2017/0143901 A1 | 5/2017 | Tubb |
| 2017/0147781 A1 | 5/2017 | Gondhalekar et al. |
| 2017/0165416 A1 | 6/2017 | Saint |
| 2017/0203036 A1 | 7/2017 | Mazlish et al. |
| 2017/0203038 A1 | 7/2017 | Desborough et al. |
| 2017/0213009 A1 | 7/2017 | Tubb |
| 2017/0220751 A1 | 8/2017 | Davis et al. |
| 2017/0232195 A1 | 8/2017 | Desborough et al. |
| 2017/0258992 A1 | 9/2017 | Zhou |
| 2017/0273607 A1 | 9/2017 | Facchinetti et al. |
| 2017/0274144 A1 | 9/2017 | Hayter |
| 2017/0281867 A1 | 10/2017 | Parikh et al. |
| 2017/0325736 A1 | 11/2017 | Cantwell et al. |
| 2017/0332952 A1 | 11/2017 | Desborough et al. |
| 2017/0337348 A1 | 11/2017 | Kovatchev et al. |
| 2017/0348482 A1 | 12/2017 | Duke et al. |
| 2017/0348483 A1 | 12/2017 | Duke et al. |
| 2017/0348484 A1 | 12/2017 | Duke et al. |
| 2018/0043094 A1 | 2/2018 | Day et al. |
| 2018/0043095 A1 | 2/2018 | Finan et al. |
| 2018/0055452 A1 | 3/2018 | Breton |
| 2018/0085523 A1 | 3/2018 | Mastrototaro et al. |
| 2018/0085524 A1 | 3/2018 | Mastrototaro et al. |
| 2018/0093039 A1 | 4/2018 | Estes |
| 2018/0099092 A1 | 4/2018 | Roy |
| 2018/0126073 A1 | 5/2018 | Wu et al. |
| 2018/0130551 A1 | 5/2018 | Gass et al. |
| 2018/0147349 A1 | 5/2018 | Finan et al. |
| 2018/0154076 A1 | 6/2018 | Budiman |
| 2018/0169322 A1 | 6/2018 | Chiu et al. |
| 2018/0169332 A1 | 6/2018 | Sadeghzadeh et al. |
| 2018/0169333 A1 | 6/2018 | Grosman et al. |
| 2018/0169334 A1 | 6/2018 | Grosman et al. |
| 2018/0174675 A1 | 6/2018 | Roy et al. |
| 2018/0200434 A1 | 7/2018 | Mazlish et al. |
| 2018/0200435 A1 | 7/2018 | Mazlish et al. |
| 2018/0200439 A1 | 7/2018 | Mazlish et al. |
| 2018/0200440 A1 | 7/2018 | Mazlish et al. |
| 2018/0200441 A1 | 7/2018 | Desborough et al. |
| 2018/0233221 A1 | 8/2018 | Blomquist |
| 2018/0235524 A1 | 8/2018 | Dunn et al. |
| 2018/0271455 A1 | 9/2018 | Zhong et al. |
| 2018/0272063 A1 | 9/2018 | Neemuchwala et al. |
| 2018/0272064 A1 | 9/2018 | Mcmahon et al. |
| 2018/0272065 A1 | 9/2018 | Talbot et al. |
| 2018/0272066 A1 | 9/2018 | Mcmahon et al. |
| 2018/0277242 A1 | 9/2018 | Zhong et al. |
| 2018/0277246 A1 | 9/2018 | Zhong et al. |
| 2018/0289891 A1 | 10/2018 | Finan et al. |
| 2018/0296757 A1 | 10/2018 | Finan et al. |
| 2018/0296758 A1 | 10/2018 | Hayter |
| 2019/0019277 A1 | 1/2019 | Chen et al. |
| 2019/0054237 A1 | 2/2019 | Budiman et al. |
| 2019/0151540 A1 | 5/2019 | Wilinska et al. |
| 2019/0374137 A1 | 12/2019 | Kovatchev et al. |

FOREIGN PATENT DOCUMENTS

| | | |
|---|---|---|
| JP | 2007267870 A | 10/2007 |
| JP | 2016167152 A | 9/2016 |
| WO | 2004023972 A2 | 3/2004 |
| WO | 2007116226 A2 | 10/2007 |
| WO | 2013067022 A1 | 5/2013 |
| WO | 2016061308 A1 | 4/2016 |
| WO | 2017027459 A1 | 2/2017 |
| WO | 2017123805 A1 | 7/2017 |
| WO | 2017124006 A1 | 7/2017 |

OTHER PUBLICATIONS

Bátora et al., Glucagon Administration Strategies for a Dual-Hormone Artificial Pancreas, IEEE Transactions on Biomedical Engineering (Jun. 2015) (Year: 2015).*

Henkel et la., Impact of glucagon response on postprandial hyperglycemia in men with impaired glucose tolerance and type 2 diabetes mellitus, 54 Metabolism Clinical and Experimental 1168-1173 (Year: 2005).*

Brod et al., Understanding Post-Prandial Hyperglycemia in Patients with Type 1 and Type 2 Diabetes: A Web-based Survey in Germany, the UK, and USA, 7 Diabetes THer 335-348 (Year: 2016).*

Beneyto and Vehi, Closed-loop blood glucose control using insulin and carbohydrates in front meals and exercise, 50(1) IFAC-Papersonline 2058-2063 (Jul. 2017) (Year: 2017).*

International Search Report and Written Opinion issued in International Application No. PCT/US2018/065619, mailed on Mar. 28, 2019, 21 pages.

Atlas, et al., "MD-Logic Artificial Pancreas System", Diabetes Care, vol. 33, No. 5, pp. 1072-1076, May 2010.

Bayard, et al., "A Bayesian Approach to Tracking Patients Having Changing Pharmacokinetic Parameters", Journal of Pharmacokinetics and Pharmacodynamics, vol. 31, No. 1, pp. 75-107, Feb. 2004.

Bleris, et al., "Implementation of Model Predictive Control for Glucose Regulation on a General Purpose Microprocessor", Proceedings of the 44th IEEE Conference on Decision and Control and the European control Conference 2005, Seville, Spain, Dec. 12-15, 2005, pp. 5162-5167.

Bolderman, et al., "Putting Your Patients on the Pump", Chapter 5, Pump Start-Up, Pump Start Basics: Patient and Prescriber Responsibilities, pp. 90-148, American Diabetes Association.

Breton, et al., "Fully Integrated Artificial Pancreas in Type 1 Diabetes; Modular Closed-Loop Glucose Control Maintains Near Normoglycemica", Diabetes, vol. 61, pp. 2230-2237, Sep. 2012.

(56) References Cited

OTHER PUBLICATIONS

Brownlee, "What is the Difference Between a Parameter and a Hyperparameter?", Machine Learning Mastery, Jul. 26, 2017, 2 pages.

Castle, "Novel Use of Glucagon in a Closed-Loop System for Prevention of Hypoglycemia in Type I Diabetes", Diabetes Case, vol. 33, No. 6, Jun. 2010.

Cescon, et al., "Early Detection of Infusion Set Failure During Insulin Pump Therapy in Type 1 Diabetes", Journal of Diabetes Science and Technology, vol. 10, No. 6, pp. 1268-1276, 2016.

Chakrabarty, et al., "Event-Triggered Model Predictive Control for Embedded Artificial Pancreas Systems", IEEE Transactions on Biomedical Engineering, vol. 65, No. 3, pp. 575-586, Mar. 2018.

Chase, et al., "Post-Prandial Glucose Excursions Following Four Methods of Bolus Insulin Administration in Subjects with Type 1 Diabetes", Diabetes UK, Diabetes Medicine, vol. 19, pp. 317-321.

Clarke, et al., "Closed-Loop Artificial Pancreas Using Subcutaneous Glucose Sensing and Insulin Delivery and a Model Predictive Control Algorithm: Preliminary Studies in Padova and Montpellier", Journal of Diabetes Science and Technology, vol. 3, No. 5, pp. 1031-1038, Sep. 2009, Sep. 2009, pp. 1031-1038.

Cobelli, et al., "Artificial Pancreas: Past, Present, Future", Diabetes, vol. 60, No. 11, pp. 2672-2682, Nov. 2011.

Cobelli, et al., "Diabetes: Models, Signals, and Control", IEEE Reviews in Biomedical Engineering, vol. 2, pp. 54-96.

Cobelli, et al., "Artificial Pancreas: Past, Present, Future", Diabetes, vol. 60, Nov. 2011, Nov. 2011.

El-Khatib, et al., "Bi-Hormonal Closed-Loop Blood Glucose Control for Type 1 Diabetes", Science Translational Medicine, vol. 2, No. 27, 17 pages, Apr. 14, 2010.

Fischer, et al., "Does Physiological Blood Glucose Control Require an Adaptive Control Strategy?", IEEE Transactions on Biomedical Engineering, vol. BME-34, No. 8, Aug. 1987, pp. 575-582.

Grosman, et al., "Multi-Zone-MPC: Clinical Inspired Control Algorithm for the Artificial Pancreas", Preprints of the 18th IFAC World Congress, vol. 44, No. 1, pp. 7120-7125, Aug. 28-Sep. 2, 2011, Milano Italy.

Grossman, et al., "Zone Model Prediciutive Control: A Strategy to Minimize Hyper- and Hypoglycemic Events", Journal of Science and Technology, vol. 4, No. 4, pp. 961-975.

Haidar, , "The Artificial Pancreas: How Closed-Loop Control is Revolutionizing Diabetes", IEEE Control Systems Magazine, vol. 36, No. 5, pp. 28-47, Oct. 2016.

Heptulla, et al., "Twenty-Four-Hour Simultaneous Subcutaneous Basal-Bolus Administration of Insulin and Amylin in Adolescents with Type 1 Diabetes Decreases Postprandial Hyperglycemia", Journal of Clinical Endocrinol Metabolism, vol. 94, No. 5, pp. 1608-1611, May 2009.

Huffman, et al., "Continuous Subcutaneous Pramlintide Infusion Therapy in Patients with Type 1 Diabetes: Observations from a Pilot Study", Endocrine Practice, vol. 15, No. 7, pp. 689-695, Nov./Dec. 2009.

Hughes, et al., "Anticipating the Next Meal Using Meal Behavioral Profiles: A Hybrid Model-Based Stochastic Predictive Control Algorithm for T1DM", Computer Methods and Programs in Biomedicine, vol. 102, No. 2, pp. 138-148, May 2011.

Karlin, et al., "Duration of Infusion Set Survival in Lipohypertrophy Versus Nonlipohypertrophied tissue in Patients with Type 1 Diabetes", Diabetes Technology & Therapeutics, vol. 18, No. 7, pp. 429-435, 2016.

King, "Continuous Glucose Monitoring-Guided Insulin Dosing in Pump-Treated Patients With Type 1 Diabetes: A Clinical Guide", Journal of Diabetes Science and Technology, vol. 6, Issue 1, pp. 191-203 Jan. 2012.

Kovatchev, et al., "Control to Range for Diabetes: Functionality and Modular Architecture", Journal of Diabetes Science and Technology, vol. 3, Issue 5, Sep. 2009, Diabetes Technology Society.

Lee, et al., "A Closed-Loop Artificial Pancreas Based on Model Predicitive Control: Human-Friendly Identification and Automatic Meal Disturbance Rejection", Biomedical Signal Processing and Control, vol. 4, pp. 347-354, 2009.

Lee, et al., "Enhanced Model Predicitive Control (eMPC) Strategy for Automated Glucose Control", 55(46) Ind Eng Chem Res. 11857-11868, Nov. 23, 2016.

Lee, et al., "In Silico Evaluation of an Artificial Pancreas Combining Exogenous Ultrafast-Acting Technosphere Insulin with Zone Model Predictive Control", 7(1), J of Diabetes Science and Technology 215-226 (Jan. 2023).

Levetan, et al., "Impact of Pramlintide on Glucose Fluctuations and Postprandial Glucose, Glucagon, and Triglyceride Excursions Among Patients With Type 1 Diabetes Intensively Treated With Insulin Pumps", Diabetes Care, vol. 26, No. 1, pp. 1-8, Jan. 2003.

Magni, et al., "Model Predictive Control of Type I Diabetes: An In Silico Trial", Journal of Diabetes Science and Technology, vol. 1, No. 6, pp. 804-812, Nov. 2007, Nov. 2007, pp. 804-812.

Mendonca, et al., "Drug Delivery for Neuromuscular Blockade With Supervised Multimodel Adaptive Control", IEEE Transactions on Control Systems Technology, vol. 17, No. 6, Nov. 2009, pp. 1237-1244.

Narendra, et al., "Adaptive Control Using Multiple Models", IEEE Transactions on Automatic Control, vol. 42, No. 2, pp. 171-187, Feb. 1997.

Patel, et al., "Randomized Trial of Infusion Set Function: Steel Versus Teflon", Diabetes Technology & Therapeutics, vol. 16, No. 1, pp. 15-19, 2014.

Percival, et al., "Closed-Loop Control and Advisory Mode Evaluation of an Artificial Pancreatic B Cell: Use of Proportional-Integral-Derivative Equivalent Model-Based Controllers", Journal of Diabetes Science and Technology, vol. 2, No. 4, Jul. 2008, pp. 636-644, Diabetes technology Society.

Percival, et al., "Development of a Multi-Parametic Model Predictive Control Algorithm for Insulin Delivery in Type 1 Diabetes Mellitus Using Clinical Parameters", Journal of Process Control, vol. 21, No. 3, pp. 391-404, Mar. 2011.

Rabasa-Lhoret, et al., "Guidelines for Premeal Insulin Dose Reduction for Postprandial Exercise of Different Intensities and Durations in Type 1 Diabetic Subjects Treated Intensively With a Basal-Bolus Insulin Regimen (Ultralente-Lispro)", Diabetes Care, vol. 24, No. 4, Apr. 2001, pp. 625-630.

Ratner, et al., "Amylin Replacement with Pramlintide as an Adjunct to Insulin Therapy Improves Long-Term Glycaemic and Weight Control in Type 1 Diabetes Mellitus: a 1-Year, Randomized Controlled Trial", Diabetes Medicine, vol. 21, pp. 1204-1212, 2004.

Sherr, et al., "Mitigating Meal-Related Glycemic Excursions in an Insulin-Sparing Manner During Closed-Loop Insulin Delivery: The Beneficial Effects of Adjunctive Pramlintide and Liraglutide", Diabetes Care, vol. 39, pp. 1127-1134, Jul. 2016.

Spencer, et al., "An Electronically Controlled Piezoelectric Insulin Pump and Valves", IEEE Transactions on Sonics and Ultrasonics, vol. SU-25, No. 3, pp. 153-156, May 1978.

Swan, et al., "Effect of Age of Infusion Site and Type of Rapid-Acting Analog on Pharmacodynamic Parameters of Insulin Boluses in Youth With Type 1 Diabetes Receiving Insulin Pump Therapy", Diabetes Care, vol. 32, No. 2, pp. 240-244, Feb. 2009.

Toffanin, et al., "Artificial Pancreas: Model Predictive Control Design from Clinical Experience", Journal of Diabetes Science and Technology, vol. 7, Issue 4, pp. 1470-1483, Nov. 2013, Diabetes Technology Society.

Trevitt, et al., "Artificial Pancreas Device Systems for the Closed-Loop Control of Type I Diabetes: What Systems Are in Development? ", Journal of Diabetes Science and Technology, vol. 10, No. 3, pp. 714-723.

Vaughn, et al., "Use of Recombinant Human Hyaluronidase to Accelerate Rapid Insulin Analogue Absorption: Experience with Subcutaneous Injection and Continuous Infusion", Endocrine Practice, vol. 17, No. 6, Nov./Dec. 2011, pp. 914-921.

Wang, et al., "Automatic Bolus and Adaptive Basal Algorithm for the Artificial Pancreatic B-Cell", Diabetes Technology & Therapeutics, V. 12,No. 11, 2010, pp. 879-888.

(56) References Cited

OTHER PUBLICATIONS

Weinzimer, et al., "Effect of Pramlintide on Prandial Glycemic Excursions During Closed-Loop Control in Adolescents and Young Adults With Type 1 Diabetes", Diabetes Care, vol. 35, pp. 1994-1999, Oct. 2012.

Weinzimer, et al., "Fully Automated Closed-Loop Insulin Delivery Versus Semi-Automated Hybrid Control in Pediatric Patients with Type I Diabetes using an Artificial Pancreas", Diabetes Care, vol. 31, No. 5, pp. 934-939, May 2008.

\* cited by examiner $$P = \begin{bmatrix} \sigma IG & \sigma 1 & \sigma 2 & \sigma 2 & \sigma 3 & \sigma 4 & \sigma 5 & \sigma 5 \\ \sigma 6 & \sigma PG & \sigma 7 & \sigma 8 & \sigma 9 & \sigma 10 & \sigma 11 & \sigma 12 \\ \sigma 13 & \sigma 14 & \sigma I1 & \sigma 15 & \sigma 16 & \sigma 17 & \sigma 18 & \sigma 19 \\ \sigma 20 & \sigma 21 & \sigma 22 & \sigma I2 & \sigma 22 & \sigma 23 & \sigma 24 & \sigma 25 \\ \sigma 26 & \sigma 27 & \sigma 28 & \sigma 29 & \sigma C1 & \sigma 30 & \sigma 31 & \sigma 32 \\ \sigma 33 & \sigma 34 & \sigma 35 & \sigma 36 & \sigma 37 & \sigma C2 & \sigma 38 & \sigma 39 \\ \sigma 40 & \sigma 41 & \sigma 42 & \sigma 43 & \sigma 44 & \sigma 45 & \sigma IB1 & \sigma 46 \\ \sigma 47 & \sigma 48 & \sigma 49 & \sigma 51 & \sigma 52 & \sigma 53 & \sigma 54 & \sigma IB2 \end{bmatrix}$$

FIG. 7

CLOSED LOOP CONTROL OF PHYSIOLOGICAL GLUCOSE

RELATED APPLICATIONS

This application is a continuation of U.S. application Ser. No. 16/955,191, filed Jun. 18, 2020, issued as U.S. Pat. No. 11,901,060 on Feb. 13, 2024, which in turn is a National Stage of International Application No. PCT/US2018/065619, filed Dec. 14, 2018, which claims priority to U.S. Provisional Application No. 62/608,834, filed Dec. 21, 2017, the disclosure of which are herein incorporated by reference in their entirety.

FIELD OF THE DISCLOSURE

The present disclosure relates to the control of physiological glucose concentrations. More particularly, the present disclosure relates to closed loop systems and methods for controlling physiological glucose concentrations in a patient.

BACKGROUND

Subcutaneous insulin replacement therapy has proven to be the regimen of choice to control diabetes. Insulin is administered via either multiple daily injections or an infusion pump with dosages being informed by capillary glucose measurements made several times a day by a blood glucose meter. This conventional approach is known to be imperfect as day to day (and in fact moment to moment) variability can be significant. Further, this approach can be burdensome to the patient as it requires repeated finger sticks, a rigorous monitoring of food intake, and vigilant control of insulin delivery.

The advent of glucose measurement devices such as a continuous glucose monitor (CGM) creates the potential to develop a closed loop artificial pancreas (AP) system. An AP system uses glucose data provided by the CGM in a dosing/control algorithm executed on a controller that provides direction to an infusion pump, and the pump administers medication to the patient. Such a system has the potential to revolutionize diabetes care as it offers the possibility of better glycemic control. Additionally, such a system reduces the patient demand for vigilance and thus fosters improved quality of life.

Some existing control algorithms for artificial pancreas systems are either restricted to operating within a small range of variation (for non-adaptive controllers) or restricted to reacting slowly to abrupt changes in glucose dynamics. Some existing control algorithms generally do not include a model of insulin in a human body, while some include a model that is a single, fixed model or a slowly adapting model. These limited control algorithms may only adequately control glucose concentrations when glucose dynamics are either constant or slowly changing. Current AP systems lack a control method designed to specifically handle abrupt as well as slow variations in glucose dynamics.

SUMMARY

In Example 1, a system to control glucose in a patient is disclosed, and the system includes a medication delivery device configured to deliver a medication dose to the patient and a controller in communication with the medication delivery device and including control logic. The control logic is operative to execute a model predictive controller algorithm to determine a first medication dose, the first model predictive controller algorithm includes a plurality of model parameters having a first set of values; determine a change in at least one of a glycemic pattern and a type of medication; and execute the model predictive controller algorithm including the plurality of model parameters having a second set of values, in response to the determined change in the at least one of the glycemic pattern and the type of medication, to determine a second medication dose.

In Example 2, the system of Example 1, wherein the second set of values are different than the first set of values for the first plurality of model parameters.

In Example 3, the system of Examples 1 and 2, wherein the first-executed model predictive controller algorithm includes the plurality of model parameters with a first number of model parameters and the second-executed model predictive controller algorithm includes the plurality of model parameters with a second number of model parameters, the second number of model parameters being equal to the first number of model parameters.

In Example 4, the system of any of Examples 1-3, wherein the plurality of model parameters include at least one of an insulin sensitivity, an insulin time constant, a meal action time constant, a sensor time constant, an insulin-to-carbohydrate ratio, an input from a user interface, and a controller gain value.

In Example 5, the system of any of Examples 1-4, wherein the second set of values for the model parameters increases aggressiveness of meal bolus dosing compared to the first set of values for the model parameters.

In Example 6, the system of any of Examples 1-5, wherein the second set of values for the model parameters includes an increased physiological glucose target compared to the first set of values for the model parameters.

In Example 7, the system of any of Examples 1-6, wherein the second set of values for the model parameters includes decreased values for the insulin compartments of covariance matrices compared to the first set of values for the model parameters.

In Example 8, the system of any of Examples 1-7, wherein the second set of values for the model parameters causes an increased basal rate compared to the first set of values for the model parameters.

In Example 9, the system of Example 8, wherein the control logic is further operative to detect onset of a dawn phenomenon, wherein the second set of values for the model parameters causes an increased basal rate compared to the first set of values for the model parameters, in response to detecting the onset of the dawn phenomenon.

In Example 10, the system of any of Examples 1-9, wherein the second set of values for the model parameters causes one of increased bolus sizes, delayed insulin suspension, and earlier resumption of insulin delivery compared to the first set of values for the model parameters.

In Example 11, the system of any of Examples 1, 2 and 4-10, wherein the second set of values for the model parameters includes fewer values compared to the first set of values for the model parameters.

In Example 12, the system of any of Examples 1-11, wherein the control logic is further operative to initiate an alarm before executing the second model predictive controller algorithm.

In Example 13, the system of any of Examples 1-12, wherein the change in the glycemic pattern is determined by comparing the patient's glucose concentration values with a database's glucose concentration values.

In Example 14, the system of Example 13, wherein the database's glucose concentration values are associated with insulin pharmacokinetics.

In Example 15, the system of any of Examples 1-14, wherein determining the change in the glycemic pattern includes comparing a current glycemic pattern with a known insulin-to-carbohydrate ratio.

In Example 16, the system of any of Examples 1-15, wherein determining the change in the glycemic pattern includes delivering a pre-determined bolus along with a standardized meal and determining a patent's response to the pre-determined bolus and consumption of the standardized meal.

In Example 17, the system of any of Examples 1-16, wherein determining the change in the glycemic pattern includes comparing values in a database with one of an elapsed time from carbohydrate ingestion and insulin dosing to a maximum reduction in glucose levels, an elapsed time from carbohydrate ingestion and insulin dosing to a half-way point leading up to the maximum reduction in glucose levels, an elapsed time from carbohydrate ingestion and insulin dosing to a half-way point back to baseline following a maximum reduction in glucose levels, an area under a glucose curve over a predetermined period of time, and an area under a glucose curve divided by an area under a glucose curve of insulin delivery.

In Example 18, the system of any of Examples 1-17, wherein the control logic is further operative to determine the type of insulin in response to a comparison between a current area under a glucose curve (AUC) and a known AUC.

In Example 19, the system of any of Examples 1-18, wherein the control logic is further operative to determine the type of insulin in response to a comparison between a current area under a glucose curve (AUC) and a known AUC during a first hour after insulin delivery.

In Example 20, the system of any of Examples 1-19, wherein the control logic is operative to execute the model predictive controller algorithm at a first interval, wherein the control logic is further operative to subsequently, in response to the determined change in the glycemic pattern and/or a type of medication, execute the model predictive controller algorithm at a second interval different than the first interval.

In Example 21, the system of Example 20, wherein the second interval is shorter than the first interval upon determining that the patient is using a faster-acting insulin.

In Example 22, the system of any of Examples 1-21, wherein the control logic is operative to execute the model predictive controller algorithm at a first interval, wherein the control logic is further operative to subsequently, in response to determining a resting state of the patient, execute the model predictive controller algorithms at a second interval different than the first interval.

In Example 23, the system of Example 22, wherein the second interval is shorter than the first interval upon determining that the patient is awake.

In Example 24, the system of any of Examples 1-23, wherein the control logic is further operative to: determine a resting state of the patient in response to input from a user interface.

In Example 25, the system of any of Examples 1-24, wherein the control logic is further operative to: determine a resting state of the patient in response to a time of day.

In Example 26, the system of Example 25, wherein the control logic is further operative to: determine the resting state of the patient in response to one of detected meal patterns, lulls in glucose excursions, frequency of access to a user input, and input from a patient's wearable device.

In Example 27, the system of any of Examples 1-26, wherein the type of medicine is either an ultra-rapid insulin or a fast-acting insulin.

In Example 28, the system of Example 27, wherein the fast-acting insulin includes insulin lispro, insulin aspart, and insulin glulisine.

In Example 29, the system of any of Examples 1-28, wherein the medication delivery device is configured to deliver insulin to the patient, in response to the determined first medication dose and the determined second medication dose.

In Example 30, a system to control glucose in a patient is disclosed, and the system includes a medication delivery device configured to deliver a medication dose to the patient and a controller in communication with the medication delivery device and including control logic operative. The control logic is operative to execute a model predictive controller algorithm at a first interval to determine a first medication dose, the first model predictive controller algorithm includes a plurality of model parameters having a first set of values; determine a resting state of the patient; and execute the model predictive controller algorithm at a second interval different than the first interval, based at least in part on the determined resting state of the patient.

In Example 31, the system of Example 30, wherein the second interval is shorter than the first interval upon determining that the patient is awake.

In Example 32, the system of any of Examples 30 and 31, wherein the control logic is further operative to: determine the resting state of the patient in response to input from a user interface.

In Example 33, the system of any of Examples 30 and 31, wherein the control logic is further operative to: determine the resting state of the patient in response to a time of day.

In Example 34, the system of any of Examples 30 and 31, wherein the control logic is further operative to: determine the resting state of the patient in response to one of detected meal patterns, lulls in glucose excursions, frequency of access to a user input, and input from a patient's wearable device.

In Example 35, a system to control glucose in a patient is disclosed, and the system includes a medication delivery device configured to deliver a medication dose to the patient and a controller in communication with the medication delivery device and including control logic operative. The control logic is operative to execute a control algorithm to determine a first medication dose, the control algorithm including a first set of tunable parameters; determine a change in at least one of a glycemic pattern and a type of medication; and execute the control algorithm to determine a second medication dose using a second set of tunable parameters, in response to the determined change in the at least one of the glycemic pattern and the type of medication.

In Example 36, the system of Example 35, wherein the control algorithm is one of a model predictive controller algorithm, a proportional-integral-derivative (PID) control algorithm, and a fuzzy logic control algorithm.

In Example 37, the system of Examples 35 or 36, wherein the control algorithm is a proportional-integral-derivative (PID) control algorithm, and wherein the tunable parameters comprise at least one of a rate of change of glucose, a difference between a measured glucose level and a target glucose level, and insulin-on-board.

In Example 38, the system of any of Examples 35-37, wherein one of the tunable parameters comprises insulinon-board, and wherein the second set of tunable parameters includes an insulin-on-board that is greater or lesser than the insulin-on-board included in the first set of tunable parameters, In Example 39, the system of any of Examples 1-38, further comprising: a user interface in communication with the controller and configured to receive input from the patient.

In Example 40, the system of any of Examples 1-39, further comprising: a glucose measurement device in communication with the controller and configured to measure glucose data associated with the patient.

In Example 41, a system to control glucose in a patient is disclosed, and the system includes a medication delivery device configured to deliver a first medication dose to the patient, means for determining at least one of a change in a type of medication and a change in a glycemic pattern, and means for determining a second medication dose in response to the change in at least one of the type of medication and the glycemic pattern.

BRIEF DESCRIPTION OF THE DRAWINGS

The above-mentioned and other features and advantages of this disclosure, and the manner of attaining them, will become more apparent and will be better understood by reference to the following description of embodiments of the invention taken in conjunction with the accompanying drawings, wherein:

FIG. 7 depicts an example of a covariance matrix;

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
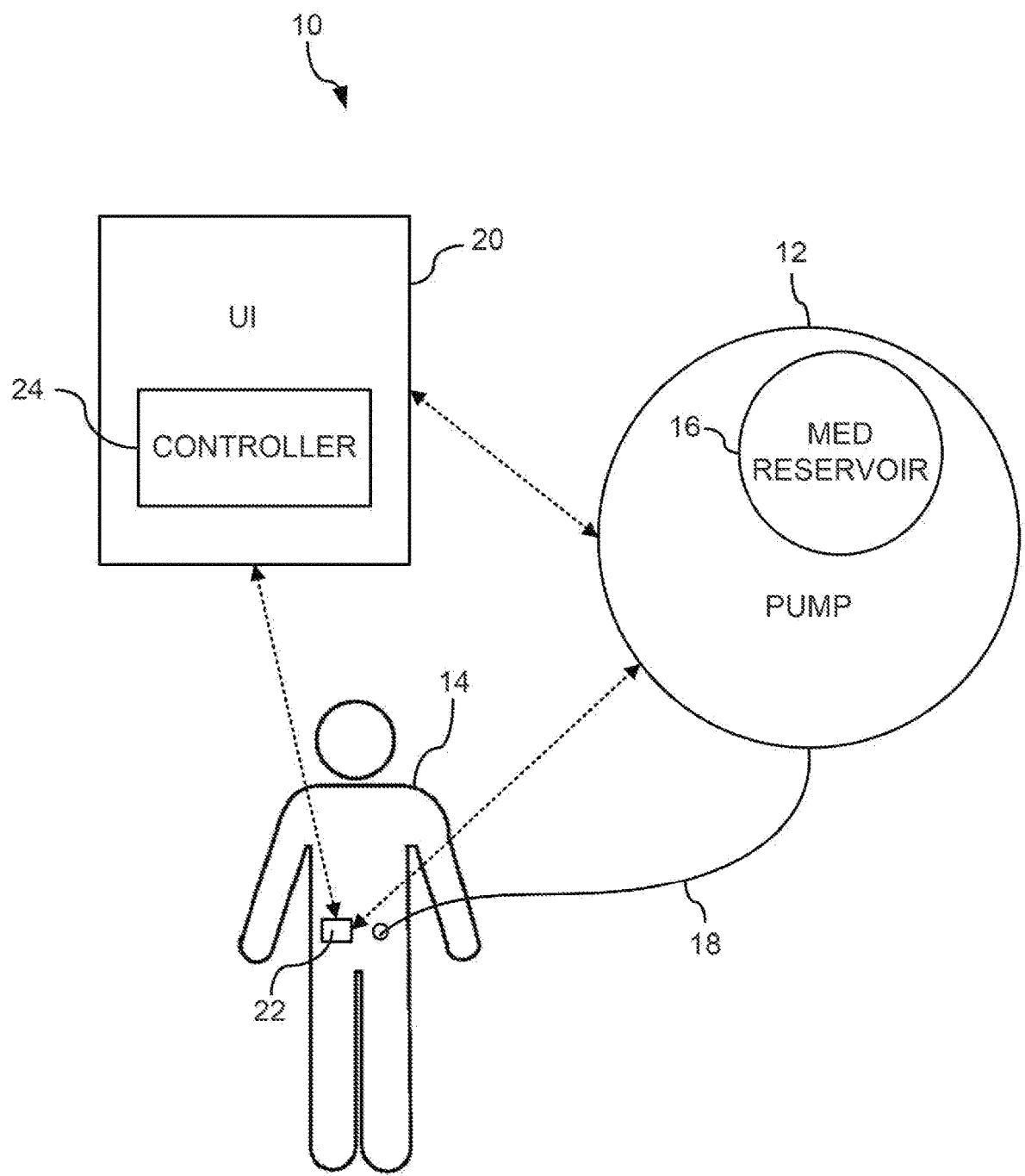
FIGS. 1 and 2 depict representational block diagrams of a system for controlling physiological glucose.

Certain embodiments of the present disclosure involve systems, methods, and devices for controlling physiological glucose concentrations in a closed loop system adaptable for use with a variety of types of medications (e.g., insulins) with a variety of pharmacokinetics. Certain embodiments of the present disclosure also involve systems, methods, and devices for controlling physiological glucose concentrations in a closed loop system that can accommodate for pharmacokinetic profiles that change over time for a given type of medication (e.g., insulin).

Different insulins will have differing pharmacokinetic profiles. For example, one type of insulin may have a pharmacokinetic profile that causes a faster reduction in blood glucose compared to a different type of insulin. Commercially-available insulins (e.g., insulin lispro, insulin aspart, and insulin glulisine) currently approved for use in pump therapy have pharmacokinetic profiles that are slower acting compared to other insulins such as ultra-rapid insulin or faster-acting insulin aspart, which attempt to closely mimic human insulin. Compared to commercially-available insulins, the faster-acting insulins (e.g., ultra-rapid insulins) are quicker at transporting from subcutaneous space to the blood stream. As such, faster-acting insulins enable more flexibility in timing of meal boluses for patients, as well as the ability to more quickly correct for errors in bolus dose calculations-thus reducing the risk of hyperglycemia. Faster-acting insulins also offer the opportunity to target tight glycemic control more aggressively for patients by increasing and/or decreasing insulin delivery at a given moment in time. Commercially-available closed loop systems are not designed to account for or are not adaptable for optimal use with pharmacokinetic profiles associated with faster-acting insulins. Certain embodiments of the present disclosure are accordingly directed to systems, methods, and devices involving closed loop systems that can accommodate for multiple types of insulins and their associated pharmacokinetic profiles in controlling physiological glucose concentrations.

Insulin pharmacokinetic profiles may change over time when continuous subcutaneous insulin is infused at a single infusion site for longer than one day. This change in pharmacokinetic profiles is sometimes referred to as the "Tamborlane Effect." A similar effect known to occur involves a gradual loss of infusion site efficacy, which may be evidenced by a rise in glucose levels that the patient is unable to correct through a usual insulin dosing regimen. This loss of efficacy is often patient specific and generally occurs over a period of four to five days, but can be longer or shorter on a patient-by-patient basis. Certain embodiments of the present disclosure are directed to controlling blood glucose and accommodating for changes in pharmacokinetic profiles over time.

System Hardware

The term "logic" or "control logic" as used herein may include software and/or firmware executing on one or more programmable processors, application-specific integrated circuits (ASICs), field-programmable gate arrays (FPGAs), digital signal processors (DSPs), hardwired logic, or combinations thereof. Therefore, in accordance with the embodiments, various logic may be implemented in any appropriate fashion and would remain in accordance with the embodiments herein disclosed.

Figure 2:
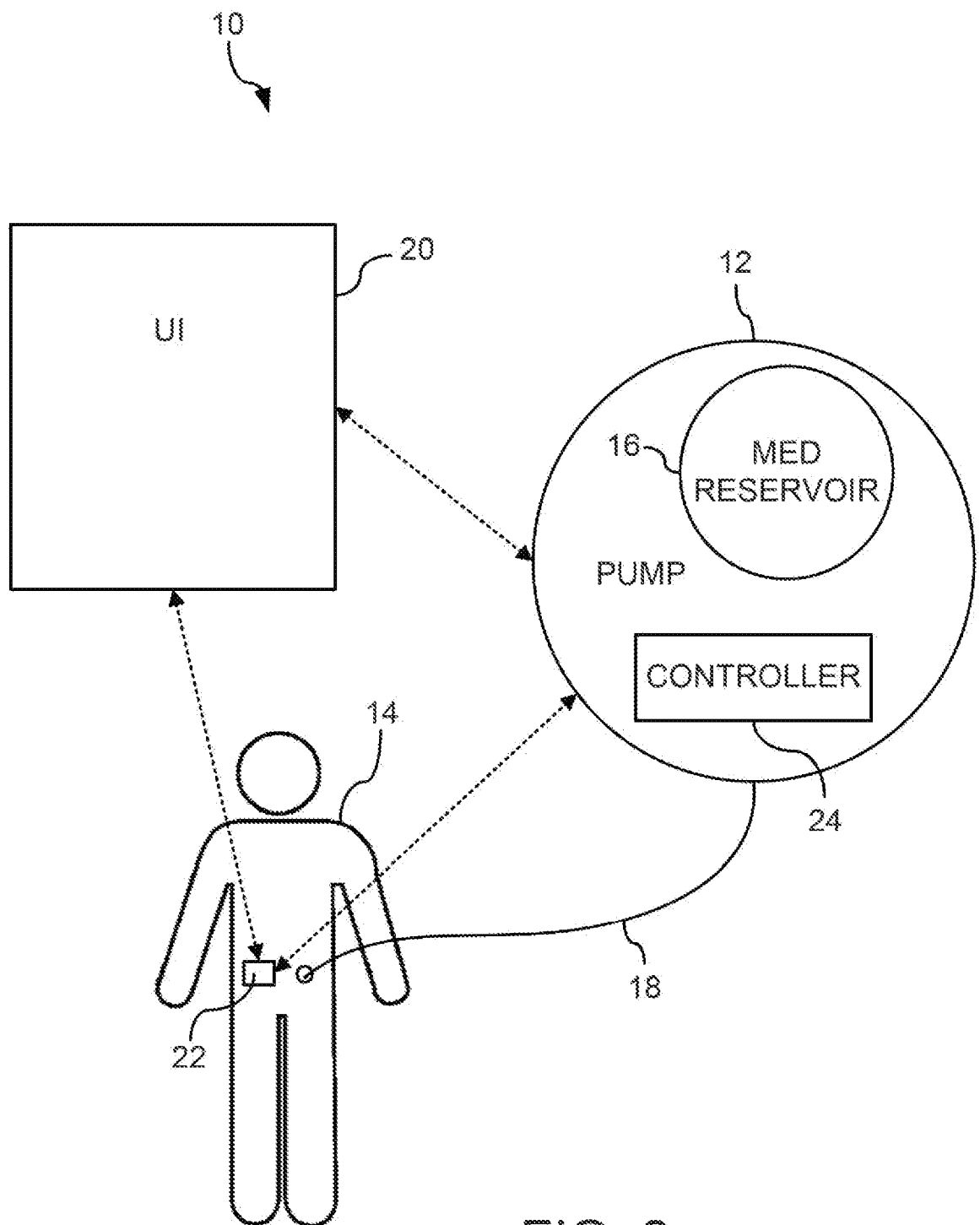

A system to provide closed-loop control of physiological glucose is disclosed herein. Exemplary hardware elements of the system include a sensor to measure the physiological glucose concentration in the body, a user interface to receive user data, a pump to deliver insulin, and an electronic controller including control logic operative to integrate the data, execute the algorithm, and control the pump. In addition, the various elements may communicate with each other. FIGS. 1-2 depict exemplary representational block diagrams of a system 10 for controlling physiological glucose. The system 10 comprises a drug delivery device 12, a user interface 20, a device to measure glucose 22, and a controller 24.

The drug delivery device 12 is illustratively an infusion pump 12. An exemplary pump 12 includes an ambulatory infusion pump such as those described in U.S. patent application Ser. No. 13/788,280, to Lanigan et al., filed Mar. 7, 2013, and entitled "Infusion Pump Assembly". The pump 12 may include at least one medication reservoir 16 which contains a first medication. The first medication may be a hormone which is involved in the control of physiological glucose. In some specific embodiments, the first medication may be a hormone which lowers physiological glucose concentrations such as insulin. In other embodiments, the drug delivery device may be used in conjunction with an oral medication such as SGLT-1 or SGLT-2. Other embodiments may include an additional reservoir 16 for a second medication which may be a hormone which is antagonistic to the first medication. For example, the second medication, stored in an additional reservoir 16, may be a drug or hormone such as glucagon which raises physiological glucose concentrations. In another example, the second medication may be another suitable glucose management drug such as GLP-1, pramlintide, amylin, or another amylin analogue. Use of the word amylin herein shall be understood to mean amylin or any analogue thereof may be used. The medication delivery device 12 may deliver at least one medication to a patient 14 via an infusion set 18 providing a fluid path from the pump 12 to the patient 14. The infusion set 18 may, for example, provide a fluid path from the pump 12 to a subcutaneous destination within the patient 14. In some embodiments, the pump 12 provides a fluid path to the subcutaneous destination within the patient 14. The pump 12 or infusion set 18 may include a needle or cannula for inserting into the subcutaneous tissue of the patient.

The system 10 includes an analyte sensor such as a glucose measurement device 22. The glucose measurement device 22 may be a standalone device or may be an ambulatory device. One example of a glucose measurement device is a continuous glucose monitor (CGM) 22. In specific embodiments, the CGM 22 may be a glucose sensor such as a Dexcom G4 or G5 series continuous glucose monitor, although any suitable continuous glucose monitor may be used. The CGM 22 is illustratively worn by the patient 14 and includes one or more sensors in communication with or monitoring a physiological space (e.g., an interstitial or subcutaneous space) within the patient 14 and able to sense an analyte (e.g., glucose) concentration of the patient 14. In some embodiments, the CGM 22 reports a value that is associated with the concentration of glucose in the interstitial fluid, e.g., interstitial glucose (IG). The CGM 22 may transmit a signal representative of an IG value to the user interface 20, the pump 12, the controller 24, or another receiver.

The system 10 includes a user interface (UI) device 20 that may be used to input user data to the system 10, modify values, and receive information, prompts, data, etc., generated by the system 10. The UI 20 may include an input device such as a keyboard or keypad for providing alphanumeric data to the controller 24. The keyboard or keypad may include tactile indicators to facilitate use without good eyesight or backlit keys for use without lighting. The UI 20 may include buttons or switches to communicate with the device. In one example, the UI 20 has buttons or switches to announce events such as a meal, start of exercise, end of exercise, emergency stop, etc. In some embodiments, the UI is a graphical user interface (GUI) with a display, where the user interacts with presented information, menus, buttons, etc., to receive information from and provide information to the system 10. The UI 20 may include a pointer, roller ball, and buttons to interact with the UI 20. Additionally, the UI 20 may be implemented on a touch screen capable of displaying images and text and capable to detecting input via a touch. The UI 20 may be a dedicated device or may be implemented via an application or app running on a personal smart device such as a phone, tablet, etc. The UI 20 may be in communication with the pump 12 and the CGM 22. The pump 12 and CGM 22 may also be in communication with one another.

The controller 24 may be included in the drug delivery device 12 (see FIG. 2) or external to the pump 12, e.g., in the UI 20 (see FIG. 1). Alternatively, the UI 20 and the pump 12 may each include a controller 24 and control of the system 10 may be divided between the two controllers 24. The controller 24 can include at least one processor (e.g., microprocessor) that executes software and/or firmware stored in memory of the controller 24. The software/firmware code contains instructions that, when executed by the processor, cause the controller 24 to perform the functions of the control algorithm described herein. The controller 24 may alternatively include one or more application-specific integrated circuits (ASICs), field-programmable gate arrays (FPGAs), digital signal processors (DSPs), hardwired logic, or combinations thereof. The controller 24 may receive information from a plurality of system 10 components and feed the information (e.g., pump data, glucose data, drug delivery data, user data) into the control algorithm which determines at least one drug delivery control parameter which may in part govern operation of the pump 12. In some specific embodiments, the controller 24 may receive pump data from the pump 12, glucose data from the CGM 22, and user data from the UI 20. In certain embodiments, the controller 24 receives user data from a device located remotely (e.g., a server, a physician's computing/communication device, and the like). The pump data received may include drug delivery data corresponding to drug dosages delivered to the patient 14 by the pump 12. The pump data may be supplied by the pump 12 as doses are delivered or on a predetermined schedule. The glucose data received by the controller 24 may include glucose concentration data from the CGM 22. The glucose data may be supplied at a continuous rate, occasionally or at predefined intervals (e.g., every 5 or 10 minutes).

The pump data, glucose data, drug delivery data, and user data may be provided to the controller 24 as acquired, on a predefined schedule or queued in memory and supplied to the controller 24 when requested. The user data may be input to the UI 20 in response to user/patient prompts generated by the UI 20 and/or declared by the patient 14 as instructed during training. In some embodiments, at least some of the pump data, glucose data, and/or user data may be retrieved from a memory associated with the controller 24, and some of this data may be retrieved from a memory in the pump 12. In some embodiments, user interaction with the UI 20 may be minimal with the patient 14 being prompted to start execution of the algorithm implemented by the controller 24 and provide meal and/or exercise announcements. In other embodiments, the user may be prompted to provide various additional data in order to initialize the algorithm implemented by the controller 24. For example, the user can input, via the UI 20, basal patterns associated with various times over a 24-hour period (e.g., a basal pattern for every 15-minute, 30-minute, 60-minute interval, etc., over the course of 24 hours). These user-inputted basal patterns can be supplemented with various boluses throughout a given 24-hour period as discussed in more detail below.

The memory of the controller 24 is any suitable computer readable medium that is accessible by the processor. Memory may be a single storage device or multiple storage devices, may be located internally or externally to the controller 24, and may include both volatile and non-volatile media. Exemplary memory includes random-access memory (RAM), read-only memory (ROM), electrically erasable programmable ROM (EEPROM), flash memory, CD-ROM, Digital Versatile Disk (DVD) or other optical disk storage, a magnetic storage device, or any other suitable medium which is configured to store data and which is accessible by the controller 24.

User data may include but is not limited to insulin/carbohydrate ratio, meal size, carbohydrate ratio of meal, and exercise. User data may also include a group of data that herein is referred to as insulin need data. The insulin need data may include but is not limited to Total Daily Insulin Dose (TDD), Total Daily Basal Dose (TDB), a basal dose, and a basal profile. In the illustrative embodiment, the TDD is the sum of all the insulin delivered over a 24-hour period, and the TDB is the sum of all the basal insulin deliveries over the 24-hour period. In one embodiment, the TDB is approximately equal to the TDD minus the sum of meal boluses. In the illustrative embodiment, the basal dose is an open loop or nominal insulin dose needed by the user for a predefined period. In one example, the basal dose is the amount of insulin needed by the user for the duration of each period or interval between glucose measurements received by the controller from the CGM. In another example, the basal dose at time t is the basal profile at time t. In the illustrative embodiment, the basal profile is a predefined time-varying insulin flow rate over the course of 24 hours. In one example, the basal profile may be expressed as a list of insulin flow rates or a paired list of flow rates and times. In another example, the basal profile may be expressed as an equation. One or more of these user data values may be updated from the UI 20 as needed. In some embodiments, the TDD and TDB are updated regularly by the controller 24, where the values are based on recorded amounts of total and basal insulin supplied to the user over one or more days. In some embodiments, TDD and/or TDB may be input by a clinician or user at the UI 20 or stored in a memory that is readable by the controller 24.

The at least one drug delivery parameter determined by the controller 24 may be a medication dose or doses, which may at least in part govern drug administration to the patient 14 via the pump 12. For insulin delivery, the drug delivery parameter may be used to compute a basal rate or micro-bolus dose, a meal bolus dose or a meal bolus dosage. In dual hormone systems, the data may inform delivery of either or both insulin and a second medication such as glucagon or amylin. In one embodiment, the drug delivery parameter provided to the pump 12 is a control signal requesting the pump 12 to deliver a specific amount or volume of medication. In one embodiment, the drug delivery parameter is an analogue or digital signal that the pump 12 converts to an amount or volume of medication or a number of pump strokes. In some embodiments, the drug delivery parameter is a deviation from the basal insulin dose or current value of the basal insulin profile. The deviation may be an amount or volume of insulin or a percentage of the basal insulin dose. Thus, the system 10 may operate in a closed loop setting which requires minimal or no interaction from the patient 14 after initial start-up to effect glycemic control.

The term physiological glucose herein refers to the measured concentration of glucose in the body. In some embodiments, physiological glucose may be the concentration of glucose in the blood, which may also be referred to as blood glucose. In other embodiments, physiological glucose may be the concentration of the glucose in the blood plasma, which may be referred to as plasma glucose. The measured value of plasma glucose is typically 10 to 12% higher than blood glucose because the blood cells of the blood have been removed in the plasma glucose determination. The relationship between plasma glucose and blood glucose depends on the hematocrit and can vary from patient to patient and over time. The physiological glucose, abbreviated herein as PG, may be measured indirectly by measuring the glucose concentration in the interstitial fluid which is referred to as interstitial glucose and abbreviated IG.

In the illustrative embodiment, the system 10 may supply insulin to the body as a basal delivery or as a bolus delivery. The basal delivery is the continuous delivery of insulin at the basal rate needed by the patient to maintain the glucose level in the patient's blood at the desired level. The pump 12 may provide the basal delivery in micro-boluses or basal doses followed by periods of zero flow that average out to the basal rate. In one example, the pump 12 supplies a basal dose at a fixed interval and the basal dose is equal to the desired basal rate times the duration of the interval. Occasionally, the user may require a larger amount of insulin due to a change in activity such as eating a meal or other activities that affect the user's metabolism. This larger amount of insulin is herein referred to as a meal bolus. A meal bolus is a specific amount of insulin that is generally supplied over a short period of time. The nature of the pump 12 may require delivering the bolus as a continuous flow of insulin for a period or as a series of smaller, discrete insulin volumes supplied over a period. The meal-bolus facilitates maintenance the glucose level as the digestive system supplies a large amount of glucose to the blood stream.

MMPC Algorithm

The Multi-Model Predictive Controller (MMPC) includes control logic of the controller 24 executing an artificial pancreas algorithm that combines multiple state vectors and their models with a model predictive control algorithm. The MMPC adds improved adaptability to changes in the body and the environment to the controller 24 by propagating multiple state vectors and selecting the state vector and its model that best matches past data. The selected-state vector and its model are then used by the controller 24 to determine the next basal rate or basal dose of insulin to deliver to the patient in order to achieve the desired physiological glucose level. The use of the multiple state vectors and their models improves the responsiveness of the algorithm to changes in metabolism, digestion, activity or other changes.

The MMPC propagates each of the state vectors at each time interval using models, glucose data and covariance matrices with a Kalman filter. In some embodiments, the MMPC retains the previous values of each state vector for a period of time and as each state vector is propagated generating the most current value of each state vector, the oldest value of each state vector is overwritten. In some embodiments, only the most current value of each state vector is stored in memory. Each state vector is associated with a unique model and unique covariance matrices. The MMPC selects a best state vector and its model based on how well the state variable for interstitial glucose (IG) matches the measured values of IG over a period in the past. The MMPC then uses in the selected-state vector and its model in a model-predictive controller where the MMPC propagates the selected-state vector out to a prediction horizon generating a predicted set of physiological glucose values over time. The set of predicted glucose values at corresponding time is herein referred to as a predicted trajectory. The MMPC uses the physiological glucose trajectory and an objective function to determine an optimal insulin trajectory with one or more limits on the insulin values.

In some embodiments, the optimal insulin trajectory is a trajectory of deviations from the basal insulin or basal profile, herein referred to as the basal-deviation trajectory. In these embodiments, the amount of insulin delivered to the body is the predefined basal insulin plus the optimal-basal deviation determined from the insulin trajectory. In these embodiments, the models do not include basal insulin inputs or endogenous glucose production. Rather, the model and the objective function consider the response of the body to meals and insulin levels above or below the predefined basal insulin rate.

A preliminary insulin rate, dose or optimal-basal deviation is taken from the value of the insulin trajectory for the first interval. The MMPC may limit this preliminary insulin rate, dose or optimal-basal deviation before passing the rate or dose request to the delivery device. In the embodiments where the optimal insulin trajectory is the deviation from the basal profile, the dose request is the sum of the limited-basal deviation plus basal profile. The limited insulin rate, limited dose, or limited-basal deviation is then fed back into the multiple state vectors in block 110A as an insulin input for the determination of the insulin rate or dose at the next interval. An example MMPC receives user data from the UI 20 and glucose concentration data from the CGM 22 and determines the amount of medication for the pump 12 to deliver to the patient 14.

Figure 3:
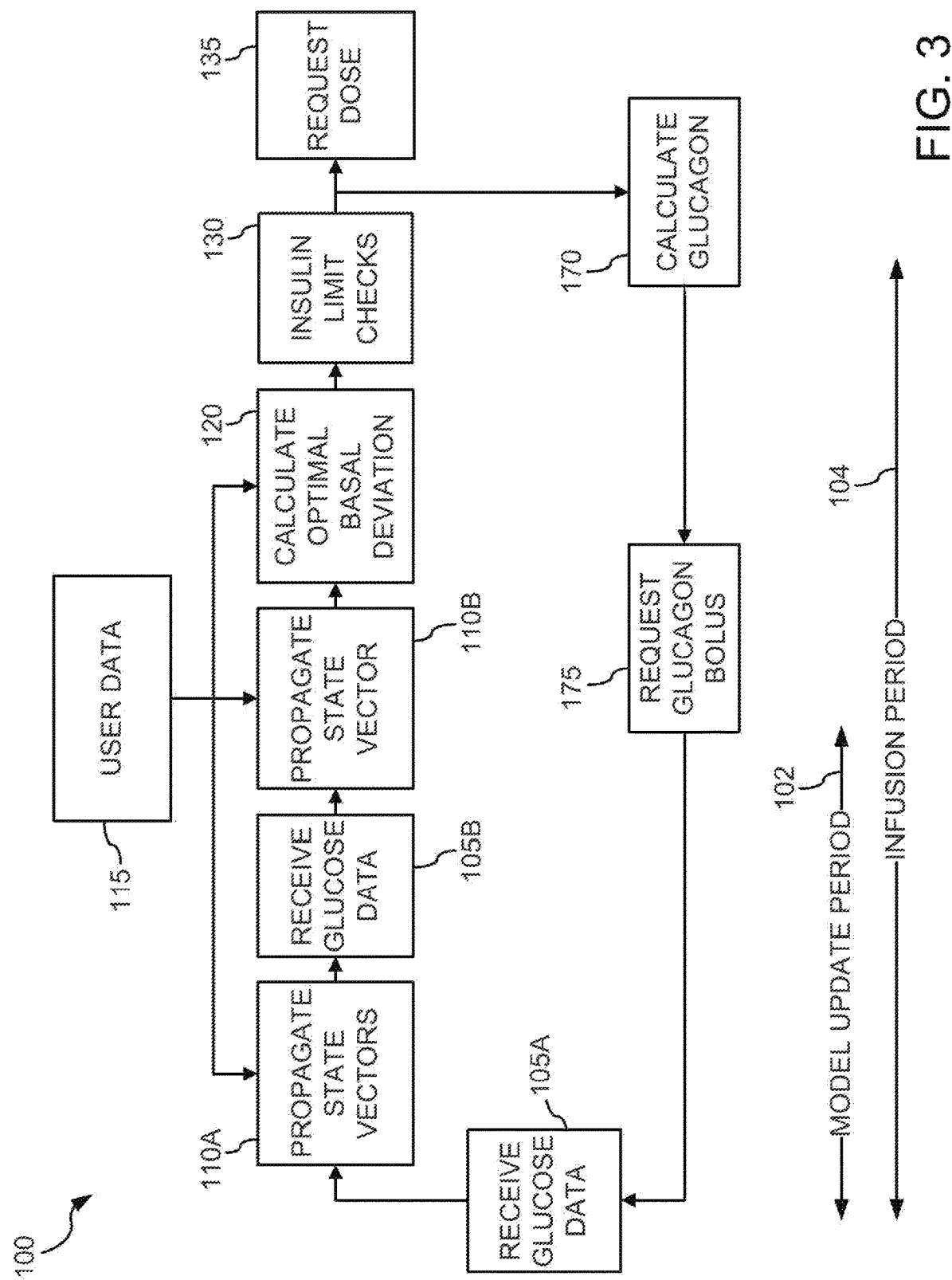
FIG. 3 depicts an example block diagram of an exemplary model predictive control algorithm configured for execution on an electronic controller of the system of FIGS. 1 and 2.
Figure 4:
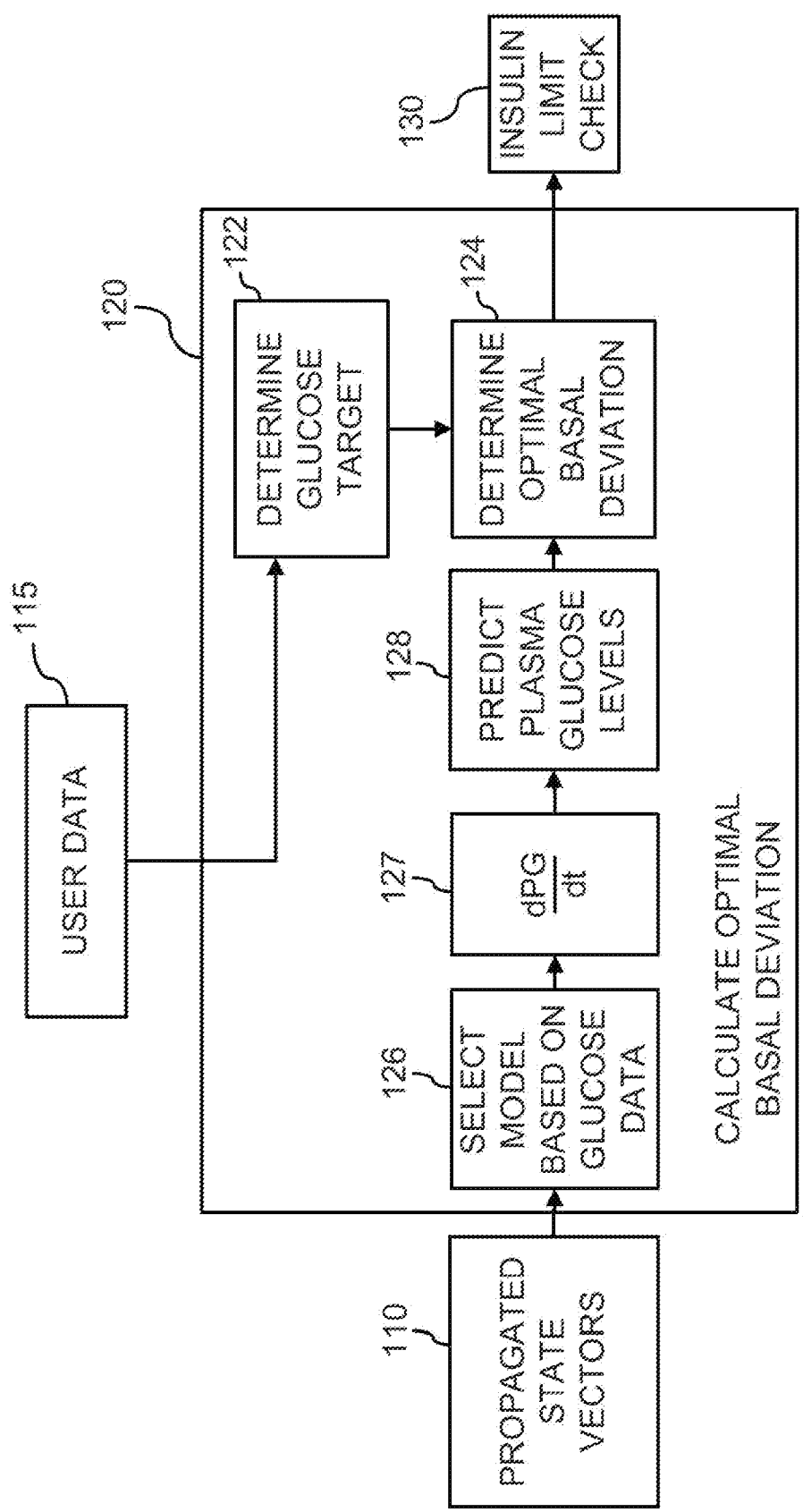
FIG. 4 depicts an example block diagram of calculating an optimal basal insulin deviation.

FIGS. 3, 4 depict representational block diagrams of an MMPC algorithm 100, which regularly receives IG data, uses one or more state-models to determine the optimal insulin dose and transmits a corresponding dose request to the insulin pump 12 before repeating the process. The MMPC algorithm 100 receives a measurement of the interstitial glucose (IG), in block 105A, from a continuous glucose monitor (CGM) placed on the patient's body or other glucose measurement device. In block 110A, the MMPC algorithm 100 propagates each state vector which includes propagating each state vector using its associated model, filtering the state vector with a Kalman filter using IG data from block 105A, and adding meal carbohydrates and meal boluses to the state vector to produce updated state vectors.

In some embodiments, the MMPC algorithm 100 follows the steps of receiving glucose data 105A and propagating the state vector 110A by determining the optimal-basal deviation in block 120. In other embodiments, the steps of receiving glucose data and propagating the state vector are repeated in blocks 105B and 110B before calculating the optimal-basal deviation in block 120. The IG data or glucose data is received 105A, 105B and an updated state vector is calculated 110A, 110B at a regular interval equal to the Model Update Period ($\tau_{UPD}$) 102. The length of the update period may be equal to the period between outputs from the glucose sensor 22.

The injection period ($\tau_{INJ}$) includes at least one set of receiving glucose data and propagating the state vectors before determining the optimal-basal deviation 120, checking the insulin limits 130 and requesting a dose 135. In embodiments where the state vector is propagated 120 once per injection period, the injection period is equal to the update period. In embodiments, where the glucose data is received twice per injection period (e.g., blocks 105A and 105B), the steps of receiving glucose data and propagating the state vectors are repeated and the injection period is equal to twice the update period. In some embodiments, the injection time is fixed and the update time may vary based on the output of CGM 22, so that the state vector may be propagated more than once between insulin deliveries or injections, if the time between receiving glucose data is shorter than the injection time. In some embodiments, if the glucose data from the glucose sensor 22 is not available or the glucose data is unreliable, the state vector will be propagated 110 without the Kalman filter step before proceeding to the determination of the optimal-basal deviation in block 120.

Block 120 determines an optimal deviation from the basal profile to control the physiological glucose of the patient, and block 135 requests the pump 12 to deliver a new insulin basal rate or dose to the patient based on the optimal deviation and the basal profile. In block 120, the MMPC algorithm 100 selects the state vector and model that has the determined best record of estimating the glucose data over a given period of time in the past. Further, in block 120, the MMPC algorithm 100 uses the selected-state vector and model in a model-predictive algorithm to determine the next optimal-basal deviation. The determination of the next optimal-basal deviation may include user data from block 115. The optimal deviation from the basal profile may be passed to block 130, where the optimal deviation may be limited by one or more rules, i.e., the value of the deviation is changed to the value of an insulin threshold, if the optimal-basal deviation exceeds that insulin threshold. The insulin thresholds or limits in block 130 may be predefined values or predetermined functions of the physiological glucose estimated by the selected-state vector. The limited-basal deviation of block 130 is then passed to block 135, where insulin dose request is determined from the sum of the limited-basal deviation and the basal profile. At block 135, the MMPC algorithm 100 transmits the insulin dose request to the pump 12 and passes the insulin dose value to block 110A for inclusion in the propagation of the next state vector. The pump 12 delivers the requested insulin dose to the patient via the infusion set 18.

FIG. 4 further illustrates an exemplary block 120 of determining the optimal-basal deviation. In block 126, the propagated state vectors and corresponding state vectors are evaluated to identify the state vector and model that best matches measured IG data over a preceding time period. In some embodiments, the measured IG data is compared to the corresponding IG values of the state vector over a fixed historical period to determine the best match between the state vector and the glucose data. In some embodiments, best match between the state vector and glucose data is based on the sum of the squared differences between the measured IG data and corresponding IG values of the state vector. In this embodiment, the squared differences are summed over time with an exponentially decaying weight. Herein corresponding estimates of IG refers to the IG value in the state vector at the time of the IG data.

In some embodiments, an identification error is calculated for each state vector at each update interval ($\tau_{UPD}$) when glucose data is received. The identification errors at each update interval are stored for each state vector. In block 126, all the identification errors of each state vector are weighted and summed over a historical period to determine a performance index for each state vector. The state vector with the lowest performance index may be selected along with at least its model for the next steps 127-124 of a model-predictive control algorithm.

In block 127, the MMPC algorithm 100 determines the current derivative of the physiological glucose with respect to time (dPG/dt). The rate of change of the physiological glucose is used in some embodiments of the MMPC algorithm 100 to set limits on insulin deliveries, determine meal boluses, determine glucagon boluses, etc. The rate of change of the physiological glucose (dPG/dt) may be determined by several methods. In some embodiments, dPG/dt is based on the most recent several (e.g., three) estimates of physiological glucose ($PG_{j-2}$, $PG_{j-1}$, $PG_j$), where a quadratic equation is fit to the three estimates and dPG/dt is set equal to the slope of the equation at j. The three most recent estimates of physiological glucose concentration may be from different state vectors depending on which state vector model was selected. In some embodiments dPG/dt is the slope of a straight-line fit to the most recent physiological glucose values ($PG_j$, $PG_{j-1}$, $PG_{j-2}$, ... $PG_{j-n}$). In some embodiments, the dPG/dt is the difference between $PG_{j-1}$ and $PG_j$, which is a slope as the time difference between successive values of $PG_j$ are constant. In some embodiments dPG/dt is difference between successive values ($PG_{j-1}$–$PG_j$) divided by the time interval ($\tau_{UPD}$).

In block 128, the selected-state vector and its model are used to predict the PG levels from the current time out to the prediction horizon ($PG_{j+1}$, $PG_{j+2}$, $PG_{j+3}$, ... $PG_{j+m}$). The period of time from current time to the prediction horizon is herein referred to as the prediction period. The prediction period may be one or more hours. In some embodiments, the prediction time is four and half hours. The predictions of future PG values are made by propagating the state vector with its model without a Kalman filter and without corrections for meals. The values of PG are predicted assuming a basal insulin dose, no insulin meal boluses and no food. In this example, the Kalman filter is not used as the future glucose data is unknown.

In block 122, the physiological glucose target ($PG_{TGT}$) is a predetermined physiological glucose concentration with corrections for meals, exercise, the measured interstitial glucose concentration and/or the physiological glucose concentration of the selected-state vector. An exemplary predetermined physiological glucose concentration is 6 milliMole/liter (mmol/L) although other suitable targets may be used.

In block 124, the optimal-basal deviation is determined for the future period from the current time to the prediction horizon. In some embodiments, the optimal basal deviation is the optimal insulin trajectory relative to the basal profile. In other embodiments, the optimal basal deviation is simply the optimal insulin trajectory. The optimal basal deviation or optimal insulin trajectory is the trajectory that minimizes one or more objective functions with one or more limits on possible insulin or deviation values. In some embodiments, the objective function sums difference between the predicted physiological glucose values and the target glucose values over the future period. In some embodiments, the objective function may also sum the basal deviations or the insulin doses over the future period. In some embodiments, the summed values may be weighted differently based on time from a meal. The cost functions and the weighting depend on one or more of the following values including, but not limited to time since meal, meal size, and exercise level. The basal insulin or insulin trajectory for the first injection period 104 may be passed as a rate or an amount to block 130, where the rate or amount may be limited based on the estimated physiological glucose, rate of change of physiological glucose and/or the past insulin deliveries by the pump 12.

The Models

A model includes a set of linear difference equations executed by control logic that calculate levels of physiological or serum glucose (PG) and the interstitial glucose (IG) in a patient's body. In some embodiments, the model comprises eight compartments that track the movement and the persistence of insulin, carbohydrates, and glucose within the body. In some embodiments, the model considers external sources of glucose (carbohydrates) and levels of insulin different from the basal profile. In these embodiments, the output of the model in the optimization step of block 124 is an optimal basal deviation ($\delta I$) from the basal insulin profile. The MMPC algorithm 100 adds the basal insulin profile value to the insulin deviation in block 135 before requesting the insulin dose from the pump 12.

The movement and persistence of insulin, carbohydrates, and glucose may be driven by several model parameters. The calculated PG values may be used to determine the next micro-bolus of insulin, a bolus of glucagon, and/or a meal bolus that may be delivered to the patient. The calculated IG may be compared to the measured IG. The MMPC algorithm 100 may comprise a large set of state vectors that each have a model with a unique combination of model parameters.

The model parameters may include but are not limited to insulin sensitivity ($S_I$), insulin time constant ($k_I$), the meal action time constant ($k_C$), sensor time constant ($k_{SENSOR}$), insulin to carbohydrate ratio (ICR). In some embodiments, the insulin sensitivity ($S_I$) is a function of the estimated basal insulin need, $S_{INS}=S_{PRM}7/I_{OL}/60$ $S_I=S_P*7/(I_{EBN}/60)$, where $S_P$ is a model parameter that controls in part, at least, the effect of insulin on physiological glucose. The estimated basal need of insulin ($I_{EBN}$) is a function of the TDD and TDB. The absorption time constant ($k_I$) is a model parameter that controls at least the rate of transport from the insulin compartments in the model. In some embodiments, the absorption time constants ($k_I$) comprise values ranging between about 30 minutes and 90 minutes. The meal action time constant ($k_C$) is a model parameter that affects at least the transport rate of carbohydrates between compartments in the model. In some embodiments, the values of the meal action time constant may range from about 30 minutes to 90 minutes. The sensor time constant (ksensor) is a model parameter that in part affects the rate of transport of glucose between the physiological compartment and the interstitial compartment. The sensor time constant may also affect the relationship between the interstitial and the physiological glucose. The insulin to carbohydrate ratio (ICR) reflects the amount of insulin required to remove a given amount of glucose from the blood. The insulin to carbohydrate value may vary from meal to meal, i.e., may have a first value for breakfast, a second value for lunch, and a third value for dinner. The model parameters may include input values at the UI 20, programmed values in the algorithm, or stored values in the memory readable by the controller 24, or a combination of these options.

Figure 5:
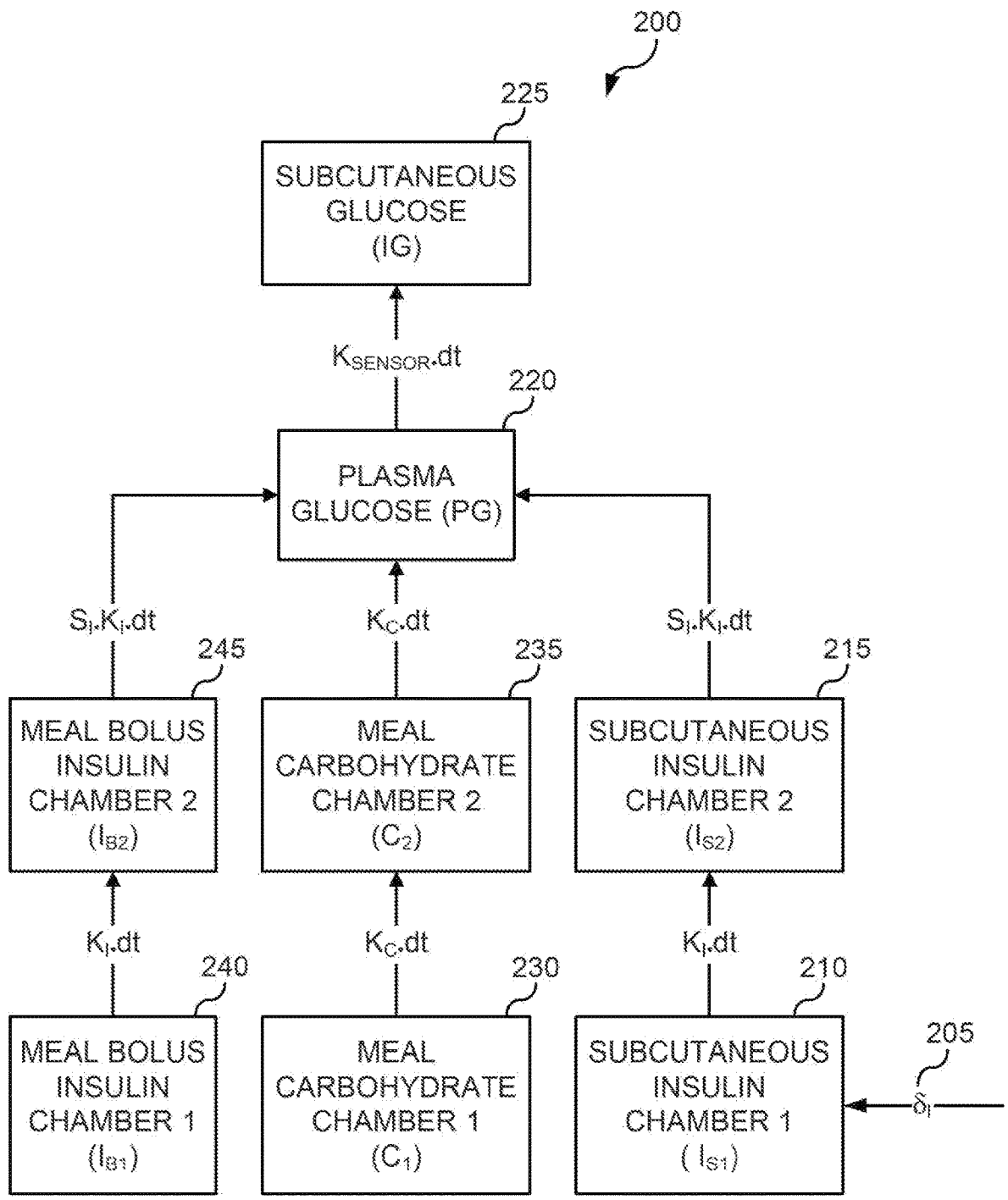
FIG. 5 depicts a block diagram of an exemplary compartmental model.

An exemplary model 200 may be represented as eight compartments that interact with each other as shown in FIG. 5. Storage and movement of insulin in the body from the subcutaneous infusion site to the blood stream may be modeled as two subcutaneous compartments 210, 215 that are connected to the blood compartment 220. Insulin microboluses may be added to the first subcutaneous chamber or compartment 210 and then transported to the second subcutaneous chamber or compartment 215, before being transported to the blood chamber or compartment 220. The modeled transport of insulin between compartments may be controlled in part by the insulin time constant ($k_I$) and the difference in insulin concentrations between the two compartments 210, 215.

Still referring to FIG. 5, the transport of carbohydrates through the stomach to the blood stream may be modeled as a first carbohydrate compartment 230 connected to a second carbohydrate compartment 235 which is connected to the blood compartment 220. The addition of carbohydrates to the first and second carbohydrate compartments is described herein. The modeled transport of carbohydrates between compartments 230, 235 may be controlled in part by the meal action time ($k_C$) and the difference in carbohydrate concentrations between the two compartments 230, 235.

Still referring to FIG. 5, the storage and movement of meal bolus insulin from the subcutaneous infusion site to the blood stream may be modeled as two meal bolus compartments 240, 245 that are connected to the blood compartment 220. The meal boluses may be added to the first and second meal-bolus chambers or compartments 240, 245, transported from the first bolus chamber 240 to the second bolus chamber 245, and then transported to the blood compartment 220. The modeled transport of insulin between compartments may be controlled in part by the insulin time constant ($k_I$) and the difference in insulin concentrations between the two compartments 240, 245.

Still referring to FIG. 5, the blood chamber or compartment 220 models the transport of the micro-bolus insulin, carbohydrates, and meal bolus insulin into the blood stream as well as the effects of insulin and carbohydrates on physiological glucose concentration. The modeled physiological glucose concentration may be controlled by the previous physiological glucose value, the insulin sensitivity ($S_I$), the insulin concentration in the second subcutaneous chamber ($I_{S2}$), the carbohydrate concentration in the second carbohydrate chamber ($C_2$), the insulin concentration in the second bolus chamber ($I_{B,2}$), the insulin time constant ($k_I$), and the meal action time ($k_C$).

The subcutaneous glucose compartment 225 models the transport of glucose from the blood stream compartment 220 to the interstitial tissue under the skin when the continuous glucose monitor (CGM) measures the glucose concentration. The modeled transport of glucose between the blood compartment 220 and the subcutaneous compartment 225 may be controlled in part by a sensor constant ($k_{SENSOR}$) and the difference in glucose concentrations between the two compartments 220, 225.

The example model described in FIG. 5 may also be described by the following set of linear difference equations:

$$\begin{aligned} IG(t+dt) &= (1 - k_{SENSOR}dt) \cdot IG(t) + k_{SENSOR}dt \cdot PG(t); \\ PG(t+dt) &= PG(t) - S_I k_I dt \cdot I_{S,2}(t) + k_C dt \cdot C_2(t) - s_I k_I dt \cdot I_{B,2}(t) \\ I_{S,2}(t+dt) &= (1 - k_1 dt) * I_{S,2}(t) + k_I dt \cdot I_{S,1}(t); \\ I_{S,1}(t+dt) &= (1 - k_I dt) \cdot I_{S,1}(t) + b_S \cdot \delta_I(t); \\ C_2(t+dt) &= (1 - k_C dt) \cdot C_2(t) + k_C dt \cdot C_1(t); \\ C_1(t+dt) &= (1 - k_C dt) \cdot C_1(t); \\ I_{B,2}(t+dt) &= (1 - k_I dt) \cdot I_{B,2}(t) + k_I dt \cdot I_{B,1}(t); \text{and} \\ I_{B,1}(t+dt) &= (1 - k_I dt) \cdot I_{B,1}(t). \end{aligned}$$ (Eqn. 1)

Each state vector is associated with a unique model that includes these equations but have a unique set of constants.

Continuing to refer to FIG. 5, the concentrations of insulin, carbohydrates, and glucose in the eight compartments can be described as the state vector $x(t)$, where $x(t)$ has the following components: $x_1(t)=IG$, $x_2(t)=PG$, $x_3(t)=I_{S2}$, $x_4(t)=I_{S1}$, $x_5(t)=C_2$, $x_6(t)=C_1$, $x_7(t)=I_{B2}$, and $x_8(t)=I_{B1}$. The state vector describes the condition of the body including the important PG and IG values at time (t). The next state vector ($x(t+\tau)$) is determined from the current state vector ($x(t)$) and the relationships described in FIG. 5.

The state space equations above may be written as a matrix equation:

$$x(t+\tau) = A_{dt}^N \cdot x(t) + B \cdot u(t) \qquad \text{(Eqn. 2)}$$

where $x(t)$ is the state vector at time t, and $x(t+\tau)$ is the state vector $\tau$ minutes later, $A_{dt}$ is a system matrix representing the equations of the model (Eqn. 1) wherein $b_s$ is zero. In one embodiment, B is a input vector that contains $b_s$ in the row for the first insulin compartment and $u(t)$ is the optimal-basal deviation ($\delta_I$). In order to propagate the state vector forward in time by the update period ($\tau_{UPD}$), the multiplication of $A_{dt} \cdot x(t)$ may be repeated N times, where $N=\tau_{UPD}/dt$, and the multiplication of $B \cdot u(t)$ may be performed. Equation 2 is exercised to advance each state vector, where each state vector has a unique model matrix, $A_{dt}$, and disturbance matrix B.

The model described in FIG. 5 and Eqn. 1 describes an exemplary embodiment of a model in the MMPC algorithm. In other embodiments, the number of model compartments may be fewer or greater than eight. In one embodiment, a minimal model is used comprising one insulin compartment and one carbohydrate compartment, where each compartment is connected to a physiological glucose chamber. This minimal model may be described by a simpler set of equations labeled Eqns. 1A:

$$\left.\begin{aligned} PG(t+dt) &= PG(t) - S_I k_I dt \cdot I_{S,2}(t) + k_C dt \cdot C_2(t) \\ I_{S,1}(t+dt) &= (1 - k_I dt) \cdot I_{S,1}(t) + b_S \cdot \delta_I(t); \text{and} \\ C_2(t+dt) &= (1 - k_C dt) \cdot C_1(t); \end{aligned}\right\} \quad \text{(Eqns. 1A)}$$

In other embodiments, another compartment may be added for bolus insulin that is modeled separately from basal insulin and the bolus insulin compartment is connected to the physiological glucose compartment. In still other embodiments, a compartment may be added to model insulin in the interstitial fluid, where this compartment is connected to the physiological glucose compartment.

Propagating the State Vector

Figure 6:
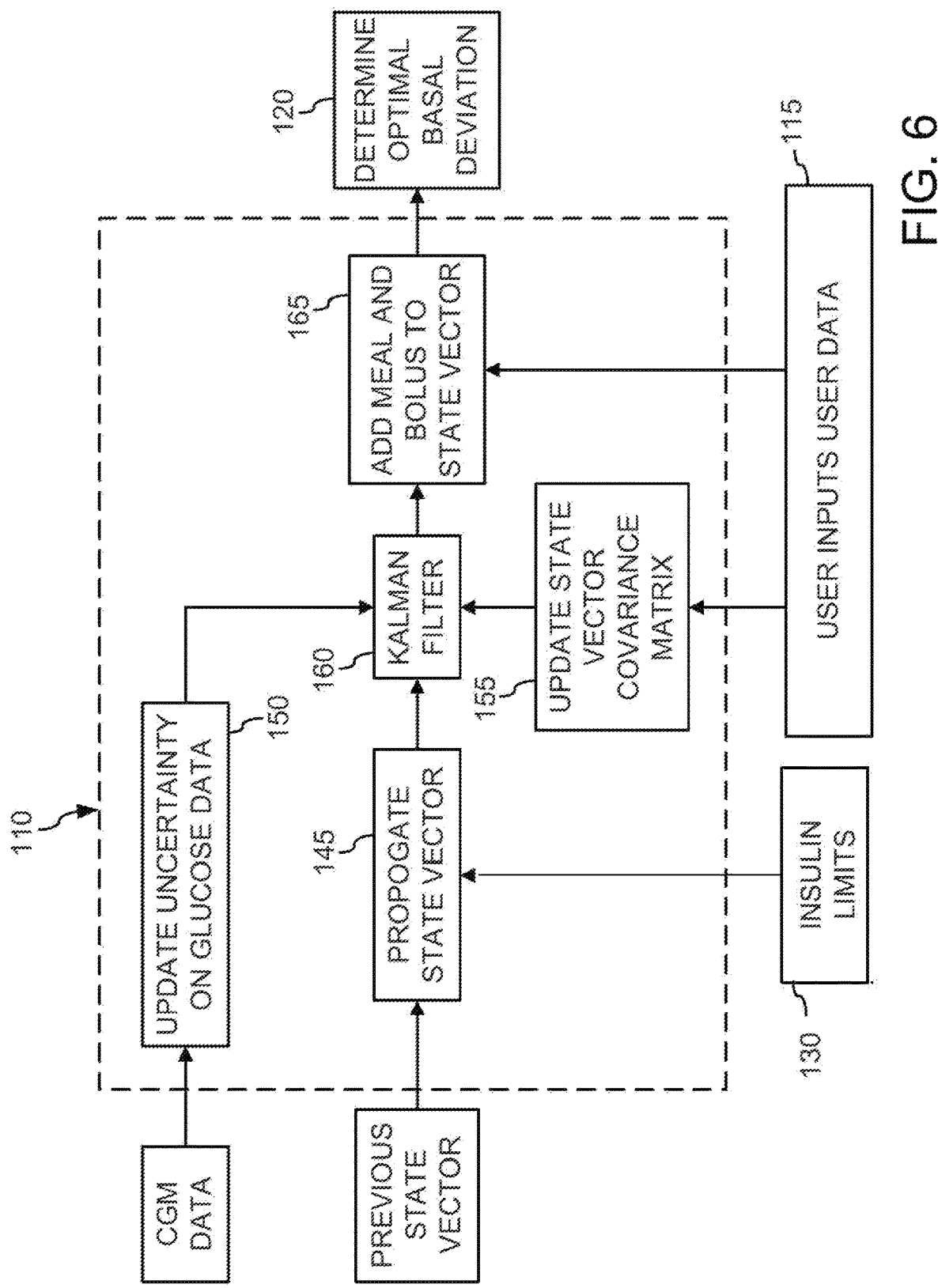
FIG. 6 depicts a block diagram of the propagation and filtering of a state vector using its associated model and covariance matrix.

FIG. 6 illustrates an exemplary schematic representation of propagating each state vector $x(t)$ to state vector $x(t+\tau)$ in the MMPC algorithm 100. Propagating each state vector $x(t)$ to state vector $x(t+\tau)$ begins by advancing each state vector $x_P(t)$ to its preliminary state vector $x_P(t+\tau)$ using the state model associated with the state vector and Eqn. 2 in block 145. Each preliminary state vector $x_P(t+\tau)$ is a preliminary estimation of the current state. If current glucose data is available from the CGM, then in block 160 each preliminary state vector $x_P(t+\tau)$ may be filtered with a Kalman filter to produce filtered state vectors $x_F(t+\tau)$. If glucose data is not available or the Kalman filter is not called, then the preliminary state vectors are passed through block 145. In block 165, the values of the bolus insulin and carbohydrate states of each preliminary state vector $x_P(t+\tau)$ or each filtered state vector $x_F(t+\tau)$ may be further corrected for a meal occurring during the most recent update period to determine the propagated state vectors $x(t+\tau)$. If a meal has not occurred during the most recent update period, then the preliminary state vector $x_P(t+\tau)$ or filtered state vector $x_F(t+\tau)$ pass through block 165 unchanged to become the propagated state vector $x(t+\tau)$. Illustratively, the references to state vectors $x(t)$ imply all the state vectors $x_j(t)$ when $j=1$ to J and J is the number of state vectors. Therefore reference to state vectors x(t), model constants such as $k_f$, $S_f$, covariance matrices P, Q, elements in the covariance matrices and performance indices $P_j(t)$. Each of these variables refer to a plurality of values such the state vectors $x_j(t)$.

In the illustrative embodiment, the MMPC algorithm 100 initializes the plurality of state vectors using one or more of the following list of parameters including, but not limited to, current time, estimate of IG, Total Daily Dose of insulin (TDD), Total Daily Basal dose (TBD), basal pattern, meal history over past four hours, insulin bolus history over past four hours and insulin-to-carbohydrate ratio (ICR). The MMPC algorithm 100 initializes the state vector with estimate of IG for the interstitial glucose value and the physiological glucose value. The carbohydrate and bolus insulin values are determined from the meal history and insulin bolus history and equations similar Eqns. 3-6 that are described below.

Referring to FIG. 6, preliminary state vectors $x_P(t+\tau)$ are filtered in block 160 with a Kalman filter to update the state variables in each preliminary state vector $x_P(t)$ based on the measured glucose data from the glucose sensor 22 and the covariance matrices P(t), Q(t), and R(t). The covariance matrix R(t) is the uncertainty of the glucose measurement and may be updated in block 150. The uncertainty of each state vector is carried in the covariance matrixes P(t) and Q(t). Each state vector is associated with unique covariance matrixes P and Q. Each covariance matrix P(t) is updated at each update interval ($\tau_{UPD}$) in block 155. The values in the covariance matrix P(t) may be further modified in block 155 based on the size and or timing of a meal.

An example of a covariance matrix P(t) is represented as matrix 300 in FIG. 7. The diagonal terms 310 list the uncertainty of the state variables in a state vector at time t. The non-diagonal terms are herein referred to as cross-correlation terms or cross terms. The cross terms list the effect of the uncertainty of one state variable on the other state variables. In one example, the uncertainty of the carbohydrates in the first compartment (first carbohydrate state variable) is the element σC1 at the fourth row and column and the uncertainty in the carbohydrates in the second compartment (second carbohydrate state variable) is the element σC2 at the fifth row and column. The non-diagonal elements in the fourth and fifth row 320 and fourth and fifth column 330 are the effects of the carbohydrate uncertainty on the uncertainty of the other body vector values including IG, PG, insulin in subcutaneous compartments 1 and 2, and insulin in bolus compartments 1 and 2. The Q(t) covariance matrix is a diagonal matrix with the initial uncertainty of each state variable along the diagonal 310 and zeros for all the cross terms. The Q(t) matrix is constant except for changes in response to meals when the MMPC algorithm 100 may change one or more values as explained below.

In block 155 each covariance matrix P(t) is advanced for the update interval per Eqn. 3:

$$P(t+\tau) = A_{dt}^N \cdot P(t) \cdot (A_{dt}^T)^N + Q(t) \quad \text{(Eqn. 3)}$$

where $A_{dt}$ is the system matrix described above. The P matrix is updated before the Kalman filter is applied to the state vector in Eqn. 4. In block 160, the preliminary state vectors, $x_P(t+\tau)$, from block 145 may be filtered with a Kalman filter when glucose data ($IG_{DATA}$) is available from the glucose sensor. The Kalman filter processes information from the glucose sensor and the uncertainty of in the data and the state variables as described in the Kalman matrix to improve the estimates of the state variables in the preliminary state vector. The Kalman matrix K(t) for each state vector is updated with the latest covariance matrix P(t) from Eqn. 3 before the preliminary state vector is filtered. The Kalman Matrix K(t) is updated per Eqn. 4:

$$K(t) = \frac{P(t) \cdot C^T}{C \cdot P(t) \cdot C^T + R} \quad \text{(Eqn. 4)}$$

where C is a unit conversion matrix and R is the uncertainty of the glucose measurement $IG_{DATA}$.variable. The filtered state vector $x_F(t)$ is calculated per Eqn. 5:

$$x_F(t) = x_P(t) + K \cdot (IG_{DATA} - IG(t)) \quad \text{(Eqn. 5)}$$

where IG(t) is the current estimate of the interstitial glucose in the preliminary state vector $x_P(t)$ and K is the Kalman matrix. Finally, the covariance matrix P is further modified after the Kalman matrix K is calculated per Eqn. 6:

$$P(t) = P(t) - K(t) \cdot C \cdot P(t) \quad \text{(Eqn. 6)}$$

In some embodiments, the symmetric diagonal covariance matrix Q(t) has an estimate of the standard deviation of error in the glucose and subcutaneous insulin for the diagonal glucose terms σIG, σPG, and subcutaneous insulin terms σI1, σI2. If the average meal time is greater than a predetermined time, then the diagonal terms in the covariance matrix Q(t) for carbohydrates (σC1, σC2) and bolus insulin (σIB1, σIB2) are zero. The average meal time is a weighted average of meals in the past predetermined time where each meal time is weighted by the amount of carbohydrates consumed at that meal. In another embodiment, the carbohydrate and bolus insulin terms in the Q(t) covariance matrix are zero if no meal occurred in the most recent predefined period. In another embodiment, the carbohydrate and bolus insulin terms in the Q covariance matrix are zero if no meal larger than a predefined amount of carbohydrates has occurred in the last predefined number of minutes. An exemplary predefined amount of carbohydrates is 5 grams, and an exemplary predefined time is 120 minutes, although other suitable thresholds may be implemented.

In one example of setting the diagonal values of the Q(t) matrix, the estimated standard deviation of error in the state variables is a percentage of the estimated insulin need ($I_{EBN}$).

In one embodiment, when a meal of a predetermined size has been consumed within a predetermined time period in the past, the diagonal terms in the Q(t) matrix for carbohydrate (σC1, σC2) and bolus insulin (σIB1 σIB2) are set to estimates of the standard deviation of error in the carbohydrate ($C_1$, $C_2$) and bolus insulin ($I_{B1}$, $I_{B2}$) values. In one example, the estimated standard deviation of error in the carbohydrate (σC1, σC2) are based on a percentage (e.g., 10%) of the sum of carbohydrates in carbohydrate compartments 1 and 2, and the estimated standard deviation of error in the bolus insulin values (σIB1, σIB2) are based on a percentage of $I_{EBN}$.

In one example, the diagonal terms for the uncertainty of the carbohydrate and bolus insulin are set to non-zero values when the sum of carbohydrates in the carbohydrate compartments exceeds a threshold (e.g., 5 grams) and the average meal time is between a low threshold (e.g., 40 minutes) and a high threshold (e.g., 210 minutes). In one embodiment, the average meal time is a weighted average of meals in the past 210 minutes where each meal time is weighted by the amount of carbohydrates consumed at that meal.

In one embodiment, when a meal has not been consumed for a predetermined amount of time, all the carbohydrate and bolus insulin terms in the covariance matrices P and Q are changed to zero. Referring now to FIG. 7, the carbohydrate terms refers to the elements in the P matrix 300 aligned with the terms σC1, σC2 and the terms σC1, σC2 (320, 330). Similarly, the bolus insulin terms in the covariance matrix P are the terms aligned with the bolus insulin terms σIB1, σIB2 and the terms σIB1, σIB2. The carbohydrate and bolus insulin terms in the Q matrix are the diagonal terms for the uncertainty of the carbohydrate and bolus insulin state variables. In one embodiment, all the carbohydrate and bolus insulin terms are set to zero in both the P and the Q matrices when a meal has not occurred for a predefined period of time. In one embodiment, the predefined period of time is 210 minutes. Setting the meal and bolus insulin values in the covariance matrices P, Q to zero may increase the likelihood of improved model stability when less than a predetermined amount of carbohydrates have been consumed within a predefined time window.

Limits on Filtered State Variables

Referring again to FIG. 6, block 160 may include one or more of corrections that limit or clip variables in the filtered state vector $x_F(t)$ resulting from applying the Kalman filter and glucose data to the preliminary state vectors. In some embodiments, the MMPC algorithm 100 limits the sum of the subcutaneous insulin state variables in the filtered state vector, $x_F(t)$ to values above a predetermined minimum insulin concentration. In one example, if the sum of insulin in all the subcutaneous compartments is less than a predetermined factor of the basal insulin, then the insulin in each compartment is increased so that the sum of the new insulin values is equal to the predetermined insulin value. In some embodiments, the values of the insulin state variables are changed so that ratio of one insulin state variable to another insulin state variable in the same state vector are unchanged. In one embodiment, the values of insulin may be increased by multiplying the insulin values by a factor. In some embodiments, the basal insulin multiplied by the predetermined insulin factor is equal to the predetermined insulin value. In one example, the predetermined factor is approximately one half the estimated basal need ($I_{EBN}$).

In some embodiments, the MMPC algorithm 100 limits the difference between preliminary or unfiltered state variables and Kalman filtered state variables for carbohydrates and bolus insulin. In some examples, if the sum of the carbohydrates in the filtered state vector is greater than a first predetermined factor of the sum of the carbohydrates in the unfiltered state vector, then the filtered values for carbohydrate are decreased so their sum is equal to the product of a second predetermined factor and the unfiltered carbohydrate sum. In one example, the first and second predetermined factors are equal.

In some embodiments, if the sum of the bolus insulin in the filtered state vector value is less than a first predetermined fraction of the sum of the bolus insulin in the unfiltered state vector, then the filtered values for bolus insulin will be increased so their sum is equal to a second predetermined fraction of the sum of the unfiltered bolus insulin values. In one example the first and second predetermined fractions are equal.

The plurality of filtered state vectors, $x_F(t+\tau)$, that have may have been corrected with the Kalman filter as described above are then passed to block 165, where the filtered state vectors are updated to include the effect of meals and the associated insulin boluses. The effects of a meal, and meal-bolus that occurred during the previous $\tau_{UPD}$ minutes are added to the filtered state vector, $x_F(t+\tau)$, in block 165 to produce the propagated state vector $x(t+\tau)$. The carbohydrates of the meal are added directly to the carbohydrate state variables in each of the state vectors. In some embodiments, where the model includes two compartments for carbohydrates the carbohydrate state variables are updated per Eqns. 7,8:

$$C_1 = C_1 + CarboRatio \cdot \exp\left(-\frac{\Delta t}{k_C}\right) \cdot MealCarbo \quad \text{(Eqn. 7)}$$

$$C_2 = C_2 + CarboRatio \cdot \left(\frac{\Delta t}{k_C}\right) \cdot \exp\left(-\frac{\Delta t}{k_C}\right) \cdot MealCarbo \quad \text{(Eqn. 8)}$$

where CarboRatio is a unit conversion factor that converts grams of carbohydrate to a concentration of carbohydrates per liter, e.g., mmols/L or μmol/L, Δt is the time between the meal and the time of the current calculation, and MealCarbo is the amount of carbohydrates in the meal.

The effects of a meal-bolus of insulin may be added directly to the insulin bolus values of the corrected updated state vector ($I_{B,1}$, $I_{B,2}$,) per:

$$I_{B,1} = I_{B,1} + S_I \cdot \exp\left(-\frac{\Delta t}{k_S}\right) \cdot Bolus \quad \text{(Eqn. 9)}$$

$$I_{B,2} = I_{B,2} + S_I \cdot \left(\frac{\Delta t}{k_S}\right) \cdot \exp\left(-\frac{\Delta t}{k_S}\right) \cdot Bolus \quad \text{(Eqn. 10)}$$

where Δt is the time between the bolus infusion and the time of the current calculation, and Bolus is an amount of insulin determined to compensate for the added carbohydrates in the variable MealCarbo of Eqns. 7, 9. In some embodiments, the value of the Bolus may not equal the bolus delivered by the pump, but rather be calculated from the amount of carbohydrates added to the carbohydrate compartments of the model. In some embodiments, using a Bolus calculated from the carbohydrates added to the model may improve model stability and improve the prediction of physiological glucose values in the future. In some embodiments, the Bolus value is calculated based on the MealCarbo and the estimated insulin basal need as, Bolus=MealCarbo/$I_{EBN}$·Fc, where Fc is a units conversion constant.

In some embodiments, block 165 further corrects state vector $x(t+\tau)$ by increasing the value of physiological glucose (PG) to reflect the appearance of glucose due to the delivery of a glucagon bolus. The correction of the PG value is defined by:

$$PG = PG + \Sigma_{i=1}^{N} g_j(t) = PG + \Sigma_{i=1}^{N} I_{GLN}^2(t-t_o(i))e^{-k_{GLN}(t-t_o} {}^{(i)}u_g(i) \quad \text{(Eqn. 11)}$$

where N is the number of previous glucagon boluses, $u_g(i)$ is the size of the glucagon boluses, to(i) is the time of glucagon bolus administration, and $k_{GLN}$ is the a transfer rate parameter representing the lag time between subcutaneous glucagon delivery and its action. The plurality of propagated, filtered and corrected state vectors, $x(t+\tau)$, is then passed out of block 110. In some embodiments, the plurality of state vectors, $x(t+\tau)$, are passed to the block 120, where the optimal basal insulin deviation is determined.

Determining Optimal Basal Insulin Deviation

Referring now to FIG. 4, the MMPC algorithm 100 in block 120 may determine the optimal basal insulin deviation by selecting the state vector and its model that best matches past interstitial glucose data ($IG_{DATA}$) from the CGM data (block 126), using the selected-state vector and its model to predict the glucose concentration throughout the following predictive period to the prediction horizon (block 128), and determining the optimal deviation from the basal profile over the predictive period in block 124 based an objective function, the glucose target determined in 122, the basal profile from 115, and one or more limits on insulin delivery rates described herein. A volume of insulin equal to the insulin trajectory for first infusion period is passed to block 130 as the optimal-basal deviation from the basal profile.

In block 126, the MMPC algorithm 100 selects the state vector and its model that best matches the glucose data or $IG_{DATA}$ values over the historical period. In some embodiments, the $IG_{DATA}$ values are measured by the CGM 22 placed on the user's body. In other embodiments, the glucose data is measured with a glucose sensor. In one embodiment, an identification error $e_j(t)$ is calculated for each state vector at each update interval as the difference between the each state variable, $IG_j(t)$ with the $IG_{DATA}$ at time t. A performance index $P_j(t)$ is then calculated for each state vector j which sums the identification errors, $e_j(t)$ over a period of time. In some embodiments, the performance value, $P_j(t)$ is the sum of the weighted and squared identification errors over a moving window in time (e.g., 2 hours or other suitable windows). In some embodiments, the weighting increases for more recent identification errors.

In one embodiment, the performance value is the weighted sum of the squared errors, where the weighting is an exponential decay function that gives more weight to more recent data. In one embodiment, the performance value for each model j is defined as:

$$P_j(t) = a \cdot e_j(t)^2 + \Sigma_{i=1}^M b^2 e^{-ci} e_j(i)^2 \qquad \text{(Eqn. 12)}$$

where a and b are constants that determine the contribution of instantaneous and long-term accuracy to the index, the error $e_j(t)$ is the difference between the measured and determined IG value for model j at the current time t and $e_j(i)$ is a vector of the previous error values of the $j^{th}$ model $e_j(i) = \{e_j(1), e_j(2), \ldots e_j(M)\}$ M is the number of stored error values in error vector $e_j(i)$ in the moving window for each state vector and model j, c is a constant defines the exponential decay function used to weight the error $E_j(i)$. In some embodiments, the use of the performance index to select the state model increases the likelihood of stability in the MMPC algorithm 100.

The MMPC algorithm 100, in block 126, may select the state vector and model with the lowest current value performance value Pj(t) and pass the selected-state vector and model on to block 128.

In some embodiments, after meal time a subset of the state vectors are considered in block 126 to identify the best match to past IG data. In some embodiments, the subset of considered state vectors contain only those state vectors whose model have relatively faster insulin absorption values. The state vectors associated with models that have relatively slower insulin absorption times are excluded from consideration to determine the state vector with the best fit to past IG data. In some embodiments, the MMPC algorithm 100 limits the state vectors considered in block 126 to state vectors associated with models with insulin absorption times less than a first insulin absorption threshold. An exemplary first insulin absorption threshold is about one hour or other suitable thresholds.

The MMPC algorithm 100 in block 128 advances the state vector selected in block 126 using the model associated with the selected-state vector to predict the physiological glucose concentration, PG(t) out to the prediction horizon. The period from the current time to the prediction horizon is herein referred to as the prediction period. In some embodiments, the selected-state vector is advanced under steady state conditions where no meal inputs and no meal insulin boluses occur. In some embodiments, the selected-state vector is advanced assuming a basal insulin dosage. Basal insulin dosage may be a zero basal deviation, a basal profile or a constant basal dose. In a preferred embodiment, the selected-state vector is advanced assuming a zero basal deviation, no meals and no insulin boluses during the prediction period. Block 128 passes the resulting predicted physiological glucose concentration values $PG_{P,I}$ to block 124, where the optimal insulin deviation from the basal profile value is determined.

The example MMPC algorithm 100, in block 124, determines the optimal deviations from the basal profile assuming no meals over the prediction period. The optimal deviations from the basal profile may be a sequence of insulin dose deviations over the prediction period that minimizes an objective function. In some embodiments, the objective function comprises the weighted-squared-glucose difference at each time step over the prediction period. The glucose difference is the difference between the target glucose values and the value of the predicted physiological glucose state variable. The objective function may further comprise the sum of weighted-squared-insulin basal deviation ($\delta_I$) at each time step over the prediction period. In some embodiments, the objective function may further comprise the sum of weighted insulin doses at each time step. Each time step may be equal to the update period ($\tau_{UPD}$) or the injection period ($\tau_{INJ}$). The weighing of either the glucose difference or the insulin doses may be a function of the time or may vary with time after a meal. In one embodiment, the objective function comprises both glucose differences and the basal deviations per Eqn. 13:

$$\text{Cost} = \Sigma_{i=1}^{ph} [w_G(i) \cdot (PG(i) - PG_{TGT}(i))^2 + K_{INSULIN} \cdot \delta_I(i)^2] \qquad \text{(Eqn. 13)}$$

where $K_{INSULIN}$ is a weighting factor for deviations from the basal insulin dosage, ph is the number of samples or predictions encompassed by the prediction period and the weighting function, $w_G(i)$, may vary over the prediction period. In some embodiments, the weighting function may give significantly more weight to the final difference between the predicted physiological glucose, PG(ph), and the target glucose $PG_{TGT}(ph)$. Further, in some embodiments the final weighting, $w_G(ph)$, is larger than the sum of the previous weighting values $w_G(1)$ through $w_G(ph-1)$. In some embodiments, the weight function, $w_G(i)$, may be reduced for periods after meals. Further, in some embodiments the weight function, $w_G(i)$, may be a nominal value for intervals greater than a meal period and much less than the nominal value for intervals less than the meal period. In some embodiments, the weight function may be less than 1% of the nominal value for a first half of the meal period after a meal and increasing from less than 1% of the nominal value to the nominal value during the second half of the meal period after a meal. In some embodiments the meal period is greater than 3 hours. The target glucose number, $PG_{TGT}(i)$, may be a function some of, but not limited to, a prescribed target glucose value, exercise, time after a meal.

Limits on Insulin Deviations in the Optimization Process

The minimizing of the cost function above is further constrained by limits on the values of the insulin deviation, $\delta_I(i)$. The limits on the insulin deviation, $\delta_I(i)$, may, for example, be based on the open loop insulin rate, $I_{OL}$. The insulin deviation may be limited so that the insulin dose remains between 0 and IMAX. Therefore the insulin deviation, $\delta_I(i)$, is limited to the range:

$$-I_{OL} \leq \delta_I(i) \leq I_{MAX}(i) - I_{OL} \qquad \text{(Eqn. 14)}$$

where $I_{OL}$ is defined below and $I_{MAX}(i)$ is a maximum basal dose. In one embodiment, the maximum basal dose may be a fixed value that is predefined by a user or a clinician. In another embodiment, the maximum basal dose may depend on the estimated physiological glucose value, PG, the total daily basal insulin, TDB, and/or the open-loop insulin, $I_{OL}$.

In some embodiments, the maximum basal dose, $I_{MAX}(i)$, is a function of the open loop insulin and the estimated physiological glucose value, PG. In this embodiment, the maximum basal dose may be equal to the product of a first factor and an open loop basal dose for physiological glucose values less than a first predefined glucose threshold. Similarly, the maximum basal dose may be equal to the product of a second factor times the open loop basal dose for physiological glucose values greater than a second glucose threshold predefined, wherein the second factor is greater than the first factor. The maximum basal dose may be equal to an interpolation between the first and second factor times the open loop basal dose based on the physiological glucose value for physiological glucose values between the first and second glucose thresholds. In some embodiments, the first factor is approximately 3 and the first glucose threshold is approximately 7 mmol/L. In some embodiments, second factor is approximately 5 and the second glucose threshold is approximately 12 mmol/L.

In some embodiments, the minimizing of the cost function above is further constrained by limits on the values of the insulin deviation, $\delta_I(i)$, that are listed in the section labeled Insulin Limits. The Insulin Limits listed below may be applied to the optimization process in block 124 at each time point during the prediction period by applying the predicted physiological glucose values and the rate of change of physiological glucose values at the corresponding time points in the prediction period (e.g., $\delta_I(i)$=fcn (PG(i), dPG(i)/dt)).

There are a multitude of numerical algorithms to find the set of optimal insulin deviation commands, $\{\delta_I(1), \delta_I(2) \ldots \delta_I(ph)\}$, which minimize the cost function of Eqn. 13. When the numerical algorithm finds the optimal set of insulin deviation commands in block 120, the MMPC algorithm 100 passes the optimal-basal deviation for the first update interval ($\delta_I(1)$) to block 135, where the optimal deviation is summed with basal profile to equal the next dose request.

Insulin Terms

The MMPC algorithm 100 uses a plurality of insulin values that may be grouped under the term insulin need. The insulin need in some embodiments is data entered by the patient or clinician at the UI 20. In another embodiment, the insulin need data may be stored in the memory on the UI 20, the controller 24, or the pump 12. The insulin need may include a single value or a basal profile. In some embodiments, the insulin need data comprises one or more of the following insulin values: the total daily dose of insulin (TDD); the total basal dose (TBD); the basal dose ($I_{BD}$), which is a single dose rate typically units/hour; and the basal profile ($I_{BP}(i)$), which is a list or equation that defines the basal insulin doses over a day. The basal dose may be a value input at the UI 20 by the user, or it may be calculated as a fraction of the TDD. In some embodiments, the basal dose is a basal factor times TDD divided by twenty-four, where the basal factor is less than one. In some embodiments, the factor is 0.55 or another suitable fraction. In other embodiments, the basal dose is the basal insulin is TDB divided by twenty four.

The open loop basal rate, $I_{OL}(t)$, is the input basal profile, $I_{BP}(t)$, limited by high and low limits. The $I_{OL}(t)$ equals $I_{BP}(t)$ except when $I_{BP}(t)$ is less than the low limit wherein $I_{BP}(t)$ equals the low limit. The $I_{OL}(t)$ equals $I_{BP}(t)$ except where $I_{BP}(t)$ is greater than the high limit wherein $I_{BP}(t)$ equals the high limit. In one embodiment, the low limit is half of TDB/24 and the high limit is 1.5 times TDB/24.

The estimated insulin basal need, $I_{EBN}$, is a function of the total daily dose of insulin (TDD) and the total daily basal insulin (TDB) that is used to set insulin sensitivity, initial values for covariance limits on filtered insulin values and calculation of the insulin bolus. In one example, the value of $I_{EBN}$ is a fraction of TDD/24. In another example, $I_{EBN}$ is limited by upper and lower bounds, where the upper and lower bounds are based on TDD and TDB.

The total daily dose of insulin (TDD) and total daily basal insulin (TDB) may be constants or may be updated during use. In one embodiment, TDD and TDB are predetermined values. In another embodiment, TDD and TDB are entered by a user or clinician at the user interface or communicated directly to the controller 24. In another embodiment, the TDD are updated by the controller to average insulin delivered each day over the past 2 weeks. In another embodiment, the TDB may be updated by the controller 24 to the two week average of daily basal insulin delivered. In another embodiment, the TDD and TDB represent the averages of total daily insulin and the total basal insulin respectively over the past 3 days. In another embodiment, the TDD and TDB represent respectively the averages of total daily insulin and the total basal insulin over the past 24 hours.

Target Glucose

As described above, the illustrative MMPC algorithm 100 in block 124 (FIG. 4) implemented by the controller uses a target physiological glucose value ($PG_{TGT}$) when determining the optimal deviation from the basal profile. The $PG_{TGT}$ is a fixed value in some embodiments. In other embodiments, $PG_{TGT}$ is modified from a nominal or preset value ($PG_{NOM}$) when various conditions are present or various events occur. The target physiological glucose value may be determined based on user data communicated to the system 10 via the UI's 20 inputs. Such adjustments of the target physiological glucose value may, for example, occur in response to the announcement of meals and/or exercise. The adjustments of the target glucose value may be governed at least in part by a target modification formula or may be based off predefined values to be used when the certain circumstances exist. Additionally, a target value adjustment may persist for a period after the condition or event occurs. The adjustment may be a static or fixed adjustment over this period or alter in magnitude (e.g., decrease linearly in magnitude) as the time period elapses.

Referring now to block 120 depicted in FIG. 4, the glucose target may be determined in block 122 and provided to block 124 which may then determine the optimal deviations from the basal profile as described above. Block 122 receives meal and exercise input data from block 115 and may alter the target physiological glucose value. As part of determining the optimal deviation in the basal profile in block 120 the nominal target glucose value may be adjusted from its nominal value. An exemplary nominal target glucose value is 5-6 mmol/L, although other suitable values and ranges (e.g., 5-5.5 mmol/L) may be implemented. The target glucose value may be adjusted in some embodiments if the patient 14 has announced exercise and not yet ended exercise while the MMPC algorithm 100 is determining the optimal deviation of the basal profile in block 120. In other embodiments, the target glucose value may be modified for exercise if a period of exercise has occurred for a predetermined period within a predefined time of the current time. In some embodiments, meal data may alter the target physiological glucose value if the patient 14 has announced a meal within a predefined period of the determination of the optimal-basal deviation.

An exercise announcement may modify the physiological glucose target value from a preset or nominal value to an exercise target value. In some embodiments, the exercise target value may be at or about 3 mmol/L greater than the preset or nominal target value. In some embodiments, the preset or nominal target value may be at or about 6 mmol/L and the exercise target value may be at or about 9 mmol/L.

A meal announcement or meal data may be input to a formula which increases the target value based on proximity to the meal. The formula may be arranged such that the meal has a greater effect on the target values in close temporal proximity to the meal. As the time from the consumption of the meal increases, the target value may be altered to a lesser degree. After a certain predefined time period has elapsed, the meal input data may no longer have an effect in determining any target value adjustment and a preset or nominal target value may be used. The effect of the meal event on the target physiological glucose value may change (e.g., decrease) in a linear fashion over time.

After the physiological glucose target value is set, a number of checks may be performed based on a physiological glucose target. These checks may cause a modification of the glucose target value ($PG_{TGT}$) to an altered final value in some instances.

Insulin Limit Checks

After the state vectors have been propagated and an optimal deviation from the basal profile has been determined in block 120, the controller 24 may compare or check the optimal deviations from the basal profile against one or more insulin limits in block 130 of FIG. 3. In some embodiments, a plurality of criteria may be used. The optimal deviations ($\delta_I$) from the basal profile may be altered to hold the delivered insulin within limits based on the physiological glucose or rate of change of physiological glucose of the selected-state vectors. The alteration of the optimal deviation may also be based on the total daily dose of insulin (TDD) and/or the total daily basal insulin (TDB). In some embodiments, the optimal deviations from the basal profile may be updated once or multiple times as the optimal deviations from the basal profile pass through the plurality of limit checks. The resulting limit checked optimal-basal deviation ($\delta_I$) may be then passed to the dose request block 135, where the basal dose or basal profile will be added to the checked-basal deviation to produce the requested insulin dose that is sent to the pump 12.

Figure 8:
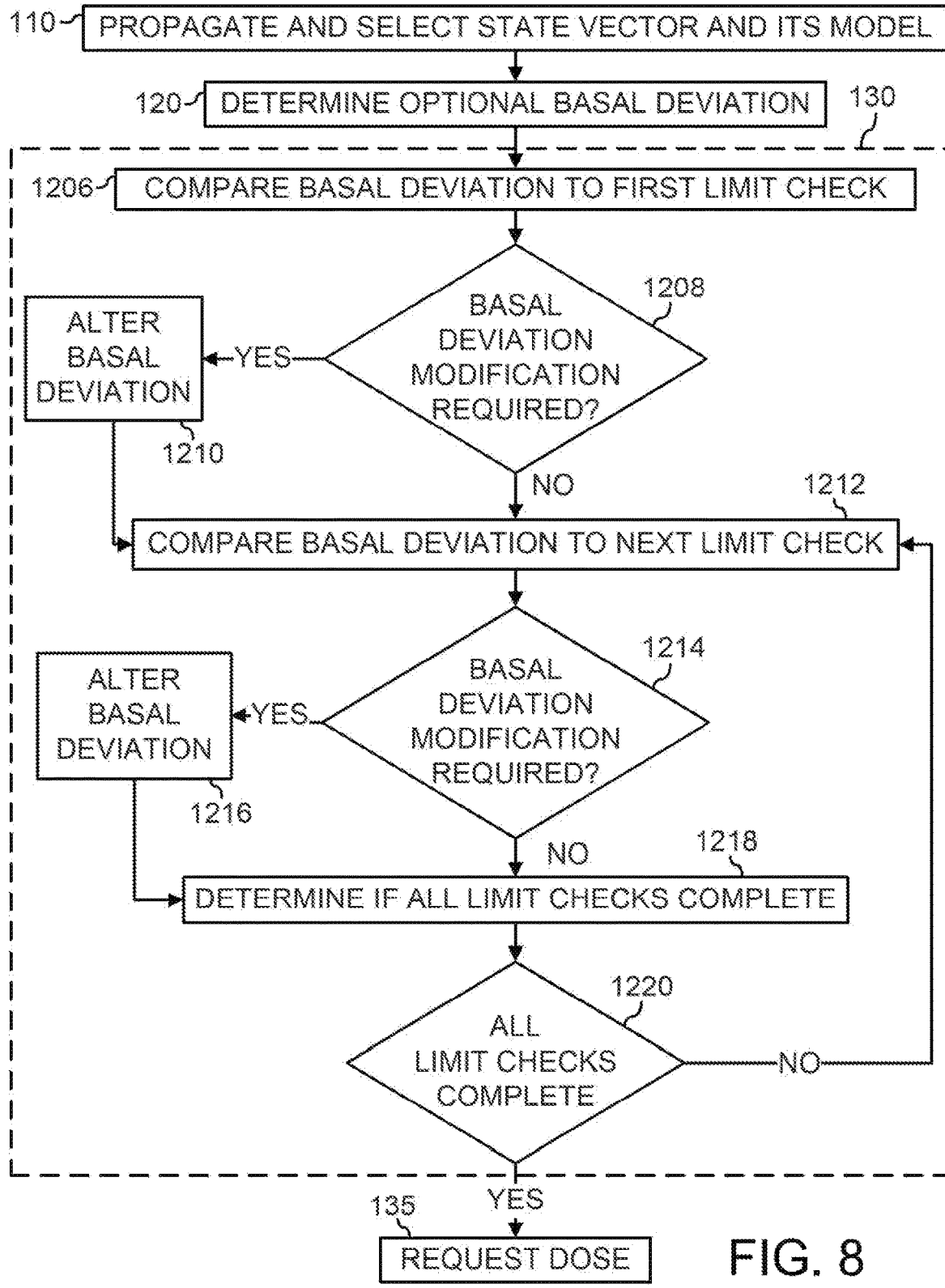
FIG. 8 depicts a flowchart which details a number of example actions which may be executed to determine if an optimal-basal deviation requires alteration.

FIG. 8 depicts an example flowchart 1200 which details a number of example actions which may be executed to determine if an optimal deviation from the basal profile requires alteration. The optimal-basal deviation from the basal profile is compared by the controller 24 to a first criteria or first limit check in block 1206. If, in block 1208, the comparison indicates no modification is needed based on the first insulin limit check, the optimal-basal deviation may be compared to a next insulin limit check in block 1212. If, in block 1208, the comparison indicates that the optimal-basal deviation requires alteration, the optimal-basal deviation may be changed to an updated-basal deviation in block 1210. The updated-basal deviation may then be compared by the controller 24 to the next insulin limit check in block 1212.

If, in block 1214, the comparison indicates that the optimal or updated-basal deviation requires alteration, the basal deviation may be updated to an updated-basal deviation in block 1216. After modification in block 1216 or if, in block 1214, the comparison indicates no modification is needed based on the insulin limit check, it may be determined whether all insulin limit checks have been completed in block 1218. If, in block 1220, all insulin limit checks have not been completed the controller 24 may return to block 1212 and perform the next insulin limit check. This may be repeated until "n" number of insulin limit checks have been made by the controller 24. In some embodiments, "n" may be up to or equal to six. If, in block 1220, all insulin limit checks have been completed, the optimal-basal deviation or updated-basal deviation may be provided as the checked-basal deviation to the pump 12, and the pump 12 may administer a micro-bolus amount of medication to the patient 14.

Equations 15-17 illustrate exemplary insulin limit checks that may be applied in block 130 of FIG. 3. In one embodiment, Eqns. 15-17 are applied sequentially to the optimal basal deviation produced by block 120. Other embodiments may include some or all of the following limits on the basal insulin deviation. These insulin limits are applied to the optimal deviation of the insulin basal profile or optimal-basal deviation ($\delta_I$) produced in block 120 in FIGS. 3, 4 to produce an updated-basal deviation that is supplied to block 135 where the delivered dose is requested from the pump 12.

In order to make the MMPC algorithm 100 respond asymmetrically to requests to deliver insulin at a rate different from the basal rate, the insulin limit block 130 in one embodiment biases changes from the basal insulin or basal profile to lower doses by increasing the magnitude of negative basal deviations and leaving positive basal deviations unchanged. If, for example, the optimal-basal deviation from block 120 is negative, then the magnitude of the optimal-basal deviation may be further increased per Eqn. 15:

$$\delta_I(i) = \delta_I(i) * F1 \text{ if } \delta_I(i) < 0 \qquad \text{(Eqn. 15)}$$

where F1 is a value greater than one. If the optimal-basal deviation is positive, the optimal-basal deviation is not changed. After increasing the magnitude of the optimal-basal deviation, if required, the controller 24 performs a next insulin limit check.

The MMPC algorithm 100 in some embodiments, assures a minimum insulin delivery when the physiological glucose is high. In some embodiments, the controller 24 limits the optimal-basal deviation to be greater than or equal to zero when the estimated physiological glucose of the selected-state vector exceeds a predetermined high glucose threshold. Holding the optimal-basal deviation at zero or above results in the delivered insulin being greater than or equal to the basal profile. In one example, the basal deviation is limited based on a high glucose threshold pre Eqn. 16:

$$\delta_I = \max(0, \delta_I) \text{ if } PG > PG_{MAX} \qquad \text{(Eqn. 16)}$$

where $PG_{MAX}$ is the high physiological glucose threshold. In one example, the high physiological threshold is at or about 13.7 mmol/L. The equation form wherein A=max(B,C) means that A is set equal to the larger value of B or C.

The MMPC algorithm 100 in some embodiments limits the insulin delivery when the physiological glucose is low. In some embodiments, the controller 24 limits the optimal-basal deviation to less than or equal to a first predetermined low value when the physiological glucose of the selected-state vector is less than a predetermined low physiological glucose threshold.

The MMPC algorithm 100 in some embodiments further limits the insulin delivery when the physiological glucose is low and dropping. In some embodiments, the controller 24 limits the optimal-basal deviation to less than or equal to a second predetermined low value when the physiological glucose of the selected-state vector is less than a predetermined low physiological glucose threshold and decreasing with time. The second predetermined low value may be less than a first predetermined low value.

The MMPC algorithm 100 in some embodiments further limits the insulin delivery when the physiological glucose is very low. In some embodiments, the controller 24 limits the optimal-basal deviation to less than or equal to a third predetermined low value when the physiological glucose of the selected-state vector is less than a second predetermined low physiological glucose threshold.

The MMPC algorithm 100 in some embodiments assures a minimum delivery of insulin over a relatively long time scale by supplying a minimum level of insulin after a predetermined period low insulin doses. In some embodiments, the controller 24 limits the insulin dose to be equal to or greater than a minimum dose when the average insulin doses over a predefined time period is below a predefined dose threshold. The average delivered insulin doses may be determined by the controller 24 by averaging the insulin doses requested by the MMPC algorithm 100 in block 135 in FIG. 3 over a predefined period. In some embodiments, the predefined period is about two hours. The delivered insulin threshold may be a small positive value. In some embodiments, the delivered insulin threshold is set at or about 0.05 units of insulin per hour.

In some embodiments, minimum long term delivery may assured by limiting the optimal-basal deviation to be equal to or greater than a first predetermined threshold, when the average delivered insulin dose over the predefined time period is less than the delivered insulin threshold. In one embodiment the first predetermined threshold value is zero, so the delivered insulin will be at least equal to the basal profile. In one embodiment this insulin limit is described in Eqn. 17:

$$\delta_I = \max(0, \delta_I) \text{ if } \frac{1}{N}\sum_{i=1}^{N} I_D(i) < I_{MIN} \qquad \text{(Eqn. 17)}$$

where $I_D(i)$ are the past requested insulin doses and IMIN is the delivered insulin threshold.

Closed Loop Control of Glucagon

In some embodiments, the system 10 may include multiple medication reservoirs 16. One medication reservoir 16 may include insulin and another reservoir may include glucagon, for example. Using data from the CGM 22, glucagon may be delivered to a patient 14 in closed loop fashion along with insulin. In some systems, administration of glucagon in addition to insulin may help to increase further the amount of time a patient 14 spends in a euglycemic state.

Glucagon delivery to a patient 14 may be controlled by a number of predefined glucagon rules which may vary depending on the embodiment. In some embodiments, the size of the glucagon bolus allotted for delivery to a patient 14 in a given day may a function of one or more of the following factors including, but not limited to: a recent meal, exercise, physiological glucose concentration, rate of change of glucose concentration, basal insulin data and an estimate of insulin on board (IOB). In some embodiments, the glucagon bolus may be may be increased if the user indicates exercise. In some embodiments, the glucagon dose may be increased during exercise. In some embodiments, the glucagon bolus may be set to zero or canceled for a period after a meal. In one embodiment, the glucagon bolus is set to zero for 120 minutes after a meal.

In some embodiments, a glucagon bolus may be delivered only when the rate of change physiological glucose (dPG/dt) is less than a glucose rate threshold ($R_{PG}$). The glucose rate threshold may be a function of the estimated physiological glucose (PG). The glucose rate threshold ($R_{PG}$) may increase inversely with the estimated physiological glucose (PG), so that the glucose rate threshold will increase with lower physiological glucose (PG) values. The controller 24 delivers glucagon as higher dPG/dt values as the PG levels decrease. In some embodiments, the glucose rate threshold is less than zero, so that glucagon is delivered only when PG is dropping faster than the glucose rate threshold. In these embodiments, the glucose rate threshold increases and has a smaller magnitude as the physiological glucose increases. In some embodiments, the glucose rate threshold may be larger than zero so that glucagon is delivered only when PG is rising slower than the glucose rate threshold. In these embodiments, the glucose rate threshold increases and has a larger magnitude as the physiological glucose increases. In some embodiments, the glucose rate threshold is less than zero for high physiological glucose values and greater than zero for low physiological glucose values. In these embodiments, glucagon is only delivered when PG is dropping faster than the glucose rate threshold at higher physiological glucose levels and at lower physiological glucose values, glucagon is only delivered when PG is rising slower than the glucose rate threshold.

The size or volume of the glucagon bolus ($Gln_B$) may scale with both the rate of change of physiological glucose (dPG/dt) and the estimated value of the physiological glucose (PG). In some embodiments, glucagon bolus with increase with rate of change of physiological glucose. In some embodiments, the amount of the glucagon bolus may increase with decreasing levels of physiological glucose concentration. In some embodiments, the glucagon bolus may increase with the amount of active insulin in the model.

Figure 9:
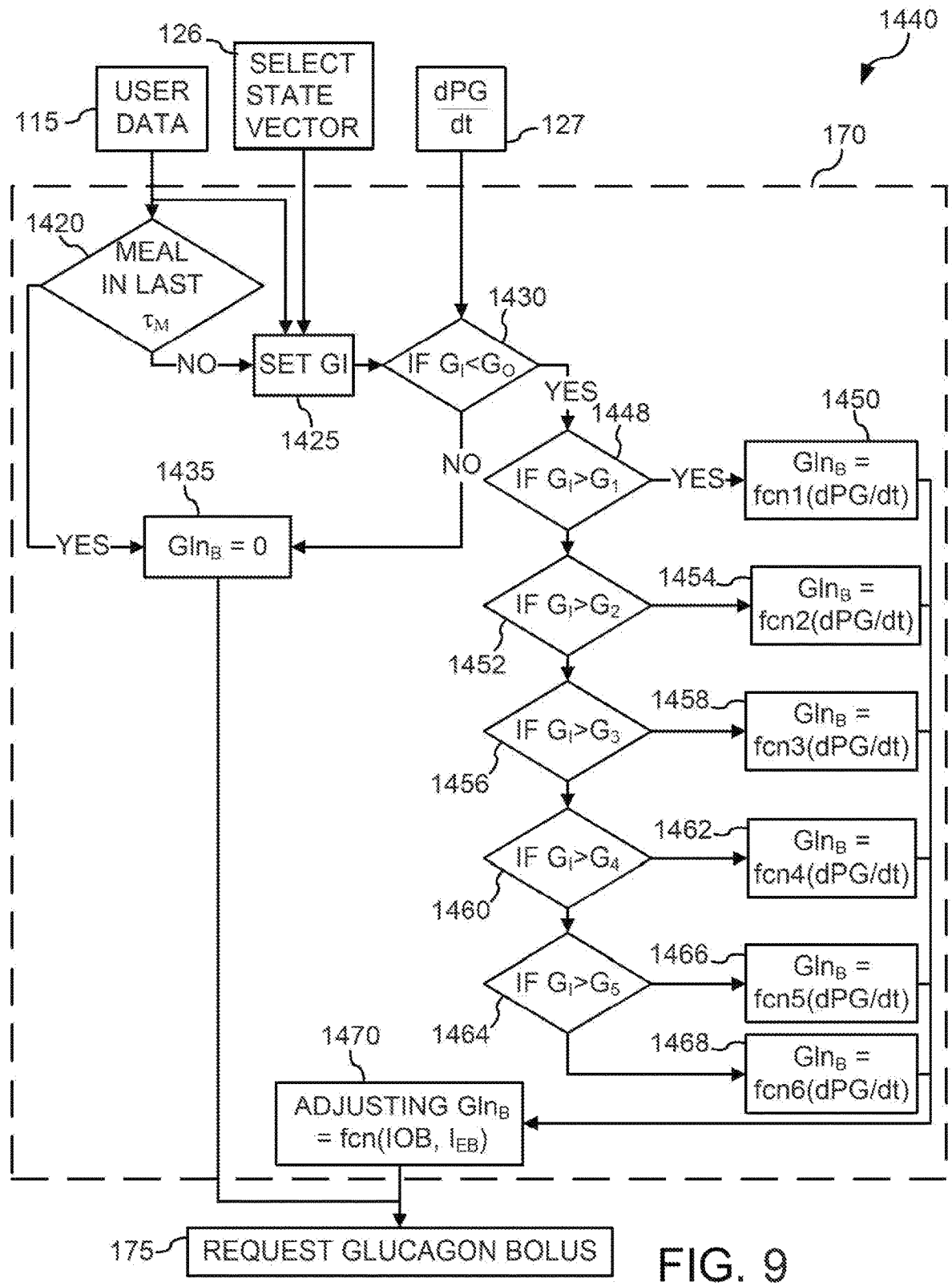
FIG. 9 depicts a flowchart detailing a number of example actions which may be executed to determine a glucagon dose.

In some embodiments, glucagon may be further or alternatively controlled by controller 24 based on the exemplary method illustrated in flowchart 1440 of FIG. 9. The controller 24 in block 170 may determine the requested bolus volume of glucagon based upon receipt of user data on meal and exercise from block 115, the current estimation of physiological glucose in the selected-state vector 126 (FIG. 4), and the rate of change of the physiological glucose (dPG/dt) from block 127. In block 1420, the controller 24 checks if a meal had been consumed within a predefined period of time ($\tau_M$). In one embodiment, $\tau_M$ is 120 minutes. If a meal had been consumed within a period of less than $\tau_M$ then the controller sets the glucagon bolus to zero in block 1435 and exits block 170. If a meal has not been consumed within the past $\tau_M$ period, then the controller determines the glucose input ($G_I$) in block 1425. The glucose input is equal to the physiological glucose (PG) of the selected-state vector 126. In some embodiments, if the user indicates exercise in block 115, the glucose input may be equal to the physiological glucose concentration minus an exercise factor. In one embodiment, the exercise factor is 3 mmol/L. The glucose input value ($G_I$) is then passed to a series of if-then-else logic decisions (e.g., blocks 1430-1468) that set the size of the glucagon bolus based on the glucose input value and the rate of change of the physiological glucose concentration determined in block 127. The resulting glucagon bolus may be updated in block 1470 as a function of the sum of insulin in the selected-state vector and the estimated basal insulin need ($I_{EBN}$).

The if-then-else logic (e.g., blocks 1430-1468) and the glucagon bolus modification 1470 are described below. In block 1430 the glucose input ($G_I$) is compared to a primary glucose threshold ($G_0$). If the input glucose is greater than the primary glucose threshold ($G_0$), then the controller sets the glucagon bolus to zero in block 1435 and exits block 170. If the input glucose ($G_I$) is less than the primary glucose threshold ($G_0$), then the controller proceeds to block 1448 and the subsequent if-then-else logic steps that set the glucagon bolus based on the estimated value and rate of change of the physiological glucose.

In block 1448, if the glucose input ($G_I$) is greater than a first glucose threshold ($G_1$), then the glucagon bolus is determined by a first function in block 1450 based on the rate of change of physiological glucose concentration (dPG/dt) or the difference of successive physiological glucose values (dy1, dy2). The difference between successive physiological glucose values [PG(i)–PG(i−1) or PG(i)–PG(i−2)] may be considered as a rate of change of physiological glucose (dPG/dt) if the successive values of physiological glucose are taken at fixed intervals. If the glucose input is less than the first glucose threshold, the logic passes to block 1452.

In the first function of block 1450, the glucagon bolus is determined based on the rate of change of glucose (dPG/dt). If the rate of change of glucose is greater than a first rate threshold ($R_{PG}1$), then the glucagon bolus is set to zero ($Gln_B=0$). After setting the glucagon bolus in block 1450, the controller 24 passes to block 1470.

In block 1452, if the glucose input ($G_I$) is greater than a second glucose threshold ($G_2$), then the glucagon bolus is determined by a second function in block 1454 based on the rate of change of physiological glucose (dPG/dt). If the glucose input is less than the second glucose threshold, the logic passes to block 1456.

In the second function of block 1454, the glucagon bolus is determined based on the rate of change of glucose (dPG/dt). If the rate of change of glucose is greater than a second rate threshold ($R_{PG}2$), then the glucagon bolus is set to zero ($Gln_B=0$). After setting the glucagon bolus in block 1454, the controller 24 passes to block 1470.

In block 1456, if the glucose input ($G_I$) is greater than a third glucose threshold ($G_3$), then the glucagon bolus is determined by a third function in block 1458 based on the rate of change of physiological glucose (dPG/dt). If the glucose input is less than the third glucose threshold, the logic passes to block 1460.

In the third function of block 1458, the glucagon bolus is determined based on the rate of change of glucose (dPG/dt). If the rate of change of glucose is greater than a third rate threshold ($R_{PG}3$), then the glucagon bolus is set to zero ($Gln_B=0$). After setting the glucagon bolus in block 1458, the controller 24 passes to block 1470.

In block 1460, if the glucose input ($G_I$) is greater than a fourth glucose threshold ($G_4$), then the glucagon bolus is determined by a fourth function in block 1462 based on the rate of change of physiological glucose (dPG/dt). If the glucose input is less than the fourth glucose threshold, the logic passes to block 1464.

In the fourth function of block 1462, the glucagon bolus is determined based on the rate of change of glucose (dPG/dt). If the rate of change of glucose is greater than a fourth rate threshold ($R_{PG}4$), then the glucagon bolus is set to zero ($Gln_B=0$). After setting the glucagon bolus in block 1462, the controller 24 passes to block 1470.

In block 1464, if the glucose input ($G_I$) is greater than a fifth glucose threshold ($G_{45}$), then the glucagon bolus is determined by a fifth function in block 1466 based on the rate of change of physiological glucose (dPG/dt). If the glucose input is less than the fifth glucose threshold, the logic passes to block 1468.

In the fifth function of block 1466, the glucagon bolus is determined based on the rate of change of glucose (dPG/dt). If the rate of change of glucose is greater than a fifth rate threshold ($R_{PG}5$), then the glucagon bolus is set to zero ($Gln_B=0$). After setting the glucagon bolus in block 1466, the controller 24 passes to block 1470.

In the sixth function of block 1468, the glucagon bolus is determined based on the rate of change of glucose (dPG/dt). If the rate of change of glucose is greater than a sixth rate threshold ($R_{PG}6$), then the glucagon bolus is set to zero ($Gln_B=0$). After setting the glucagon bolus in block 1468, the controller 24 passes to block 1470.

In the illustrated embodiment, the primary glucose threshold is greater than the first glucose threshold, the first glucose threshold is greater than the second glucose threshold, the second glucose threshold is greater than the third glucose threshold, the third glucose threshold is greater than the fourth glucose threshold, and the fourth glucose threshold is greater than the fifth glucose threshold.

In block 1470, the glucagon bolus determined in one of blocks 1450-1468 by one of the first function through the sixth function may be updated based on the active insulin in the body and the estimated basal insulin need ($I_{EBN}$). The active insulin in the body or Insulin on Board (IOB) is the sum of insulin in the insulin compartments of the selected-state vector. In one embodiment represented in FIG. 5 and Eqn. 1, the insulin compartments include the two subcutaneous compartments ($I_{S1}$, $I_{S1}$) and the two bolus compartments ($I_{B1}$, $I_{S1}$). The IOB is based on the basal deviations over time that are requested by block 120, 130 in FIG. 4. The glucagon bolus request from block 1470 or the zero request from 1435 are then passed to the glucagon bolus block 180.

Meal Bolus

Figure 10:
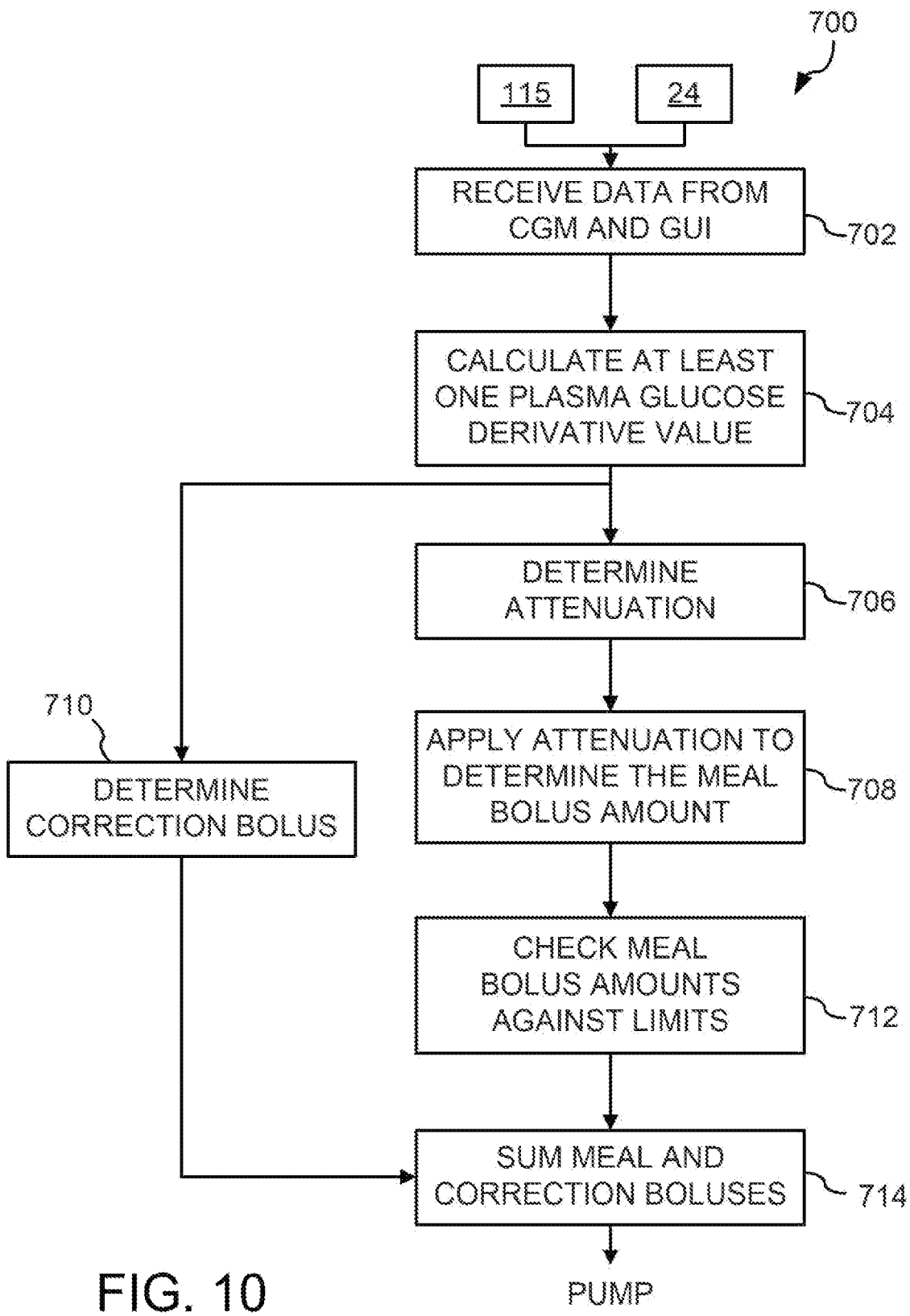
FIG. 10 depicts a flowchart detailing various example logic, which may be applied when determining an amount of drug (e.g., insulin) to be delivered in a meal bolus.

Referring now to the flowchart 700 shown in FIG. 10, various logic rules may be applied when determining an amount of drug (e.g., insulin) to be delivered in a meal bolus to the patient 14 to maintain the physiological glucose concentrations at the desired level or range during and after a meal. In block 702, the current physiological glucose concentration (PG) concentration and the meal data are received. In block 704, the controller 24 may determine at least the rate of change of the physiological glucose concentration (dPG/dt). The dPG/dt may be determined by any suitable method including the at least one method is described herein. The meal bolus is determined from the amount of carbohydrates in the meal (CHO), the insulin to carbohydrate ratio (ICR) and a bolus attenuation factor ($P_{CHO}$), where the bolus attenuation factor reduces the meal bolus when the physiological glucose is relatively low and/or decreasing in value. The closed loop control of the physiological glucose provided by the MMPC algorithm 100 provides a method to provide additional insulin to make up for the reduced meal bolus if needed to maintain euglycemia.

In one embodiment, the physiological glucose concentration values are provided directly from the CGM 22. In some embodiments, the physiological glucose concentrations are the current physiological glucose concentration of the selected-state vector as described above in relation to block 126 in FIG. 4. In another embodiment, the meal bolus algorithm uses physiological glucose values estimated from glucose measurements by the CGM 22.

Referring now to FIGS. 1-2, when determining a meal bolus, the system 10 may determine a meal bolus amount with inputs from at least one of the glucose sensor 22 and the UI 20. A preliminary value for the meal bolus may be the carbohydrate content of the meal divided by an insulin-to-carbohydrate ratio. The preliminary value for the meal bolus may be attenuated based on the physiological glucose values determined by the controller 24. The carbohydrate content of the meal may be explicitly entered at the UI 20 or may be inferred by the controller 24 from meal data supplied at the UI 20. The insulin to carbohydrate ratio may be input at the UI 20 and/or stored in memory that is readable by the controller 24. The carbohydrate content of the meal may be input by the user as a qualitative judgment of the user. For example, the user may indicate a meal size via the UI 20 of the system 10. In some embodiments, the meals size may be selected from a plurality of categories such as, but not limited to: small, medium, large, or snack.

Referring again to flowchart 700 in FIG. 10, the meal bolus (BOLM) may be calculated from the carbohydrate content of the meal (CHO), the insulin to carbohydrate ratio (ICR) and an attenuation factor. The attenuation factor depends on the physiological glucose concentration and the rate of change of the physiological glucose and determined from a predefined formula in block 706. The meal bolus is determined in block 708. In block 712, the meal bolus is limited to less than a predefined fraction of the total daily insulin (TDD) in block 712. The resulting meal bolus is passed as a delivery request to the pump 12, and the pump 12 may deliver the insulin meal bolus to the user.

The meal bolus algorithm may attenuate the meal bolus of small meals differently than larger meals. For example, if the carbohydrate content of the meal is estimated to be above a carbohydrate threshold ($C_{THD}$), then the meal bolus may be calculated as a product of the carbohydrate value (CHO), and the attenuation factor ($A_{CHO}$) divided by the insulin to carbohydrate ratio (ICR):

$$BOL_M = \frac{CHO}{ICR} \cdot A_{CHO} \text{ if } CHO > C_{THD} \quad \text{(Eqn. 18)}$$

Continuing this example, if the carbohydrate content is estimated to be less than the same carbohydrate threshold, then the meal bolus calculation may be altered to:

$$BOL_M = \max\left(0, \frac{CHO - C_{THD} * (1 - A_{CHO})}{ICR}\right) \text{ if } CHO \leq C_{THD}. \quad \text{(Eqn. 19)}$$

The equation for the meal bolus (Eqn. 19) modifies the reduction of the meal bolus for small meals by the attenuation factor ($A_{CHO}$) so that magnitude of the bolus attenuation for a given $A_{CHO}$ is constant below the carbohydrate threshold. In Eqn. 19, the magnitude of the bolus attenuation proportional to the carbohydrate content of the meal above the carbohydrate threshold and proportional to the carbohydrate threshold for smaller meals below the same carbohydrate threshold. In some embodiments, the carbohydrate threshold is 70 grams, although other suitable thresholds may be provided.

The attenuation factor, $A_{CHO}$, is a function of the physiological glucose and the rate of change of physiological glucose. The attenuation factor increases with both increases in physiological glucose and increasing rates of change of the physiological glucose. The attenuation factor may be bound by a lower value and an upper value. In some embodiments, lower limit of the attenuation factor is 0.8. In some embodiments, the upper limit on the attenuation factor is 1.0. In some embodiments, the attenuation factor can be determined from a spline fit of PG and dPG/dt to the values in Table I.

TABLE I

| | attenuation factor values | | |
|---|---|---|---|
| | dPG/dt = −3 mmol/L hr | dPG/dt = 0 mmol/L hr | dPG/dt = 3 mmol/L hr |
| PG = 4.0 mmol/L | 0.8 | 0.9 | 0.9 |
| PG = 6.5 mmol/L | 0.8 | 1.0 | 1.0 |
| PG = 9.0 mmol/L | 1.0 | 1.0 | 1.0 |

In some embodiments, the controller 24 may determine the attenuation factor from a set of linear interpolations for physiological glucose (PG) values and rate of change of physiological glucose (dPG/dt) values. The physiological glucose is may be the estimated physiological glucose (PG) determined by the CGM and/or from the selected-state vector (block 126 in FIG. 3). The rate of change of physiological glucose (dPG/dt) may be determined in several fashions. In some embodiments the rate of change of PG is 60*(PG(t)−PG(t−dt))/dt where where dt is 20 mins and dPG/dt has units of mmol/L/hr.

In the example, the meal attenuation ($A_{CHO}$) ranges from 1.0 to 0.8 with the lower attenuation values resulting when physiological glucose concentration is both low (e.g. below 6.5 mmol/L) and decreasing with time.

Referring now to FIG. 10, the attenuated meal bolus ($BOL_M$) from block 708 may be limited by in block 712 based on the total daily dose of insulin (TDD). In some embodiments, the meal bolus is limited to being equal to or less than a predetermined upper limit. If the meal bolus is greater than the predetermined upper limit, the meal bolus is set equal to the predetermined upper limit. In some embodiments, the upper limit is fraction of the TDD. In one embodiment, the upper limit is one fifth of TDD. The resulting limited meal bolus from block 712 is then passed to block 714.

In addition to the meal bolus ($BOL_M$) determined in block 708, a correction bolus ($BOL_C$) is determined in block 710 based on the estimated physiological glucose determined in block 704 as described above. In some embodiments, the correction bolus is also based on the insulin-on-board (IOB) or active insulin in the model. The IOB is the sum of the insulin state variables of the selected-state vector at the current time. The insulin state variables represent the amount or concentration of insulin in the insulin compartments of the model. In some embodiments represented in FIG. 5 and Eqn. 1, the insulin compartments include the two subcutaneous compartments ($I_{S1}$, $I_{S1}$) and the bolus compartments ($I_{B1}$, $I_{B1}$). In some embodiments, the insulin in the various compartments of the model represents the sum of insulin boluses over time plus the basal deviations over time less the insulin transported or converted in the blood compartment 220. In one embodiment, the model and the IOB do not include basal profile insulin or basal dose insulin when these are assumed to compensate for the endogenous glucose production that, in this embodiment, is also not included in the model. In some embodiments, the correction bolus is added to the limited meal bolus in block 714 and the resulting bolus is requested from the insulin delivery device 12. In other embodiments, a request for the limited meal bolus is passed to the pump 12 independently from the request for the correction bolus.

The correction bolus ($Bol_C$) varies the based on estimated physiological glucose value (PG) and the estimated insulin on board (IOB). Illustratively, the correction bolus is zero for PG values below a low PG threshold and increases with PG above the low PG threshold. The rate of increase in the value of the bolus correction with PG is reduced above a high PG threshold.

Closed Loop Control of Glucose Using Differing and/or Changing Pharmacokinetic Profiles As noted above, different insulins will have differing pharmacokinetic profiles. For example, some insulins are designed to reduce blood glucose faster than other insulins. These faster (e.g., ultra-rapid-acting) insulins are quicker at transporting from the subcutaneous space to the blood stream compared to slower (e.g., traditional fast-acting) insulins (e.g., insulin lispro, insulin aspart, and insulin glulisine). Further, insulin pharmacokinetic profiles may change over time, for example, when continuous subcutaneous insulin is infused at a single infusion site for longer than one day. And, certain patients react to insulin differently over time.

To accommodate for the differing and/or changing (e.g., progressive) pharmacokinetic profiles, the system 10, via the controller 24, can execute a first algorithm that determines an optimal dose of insulin for a patient for a given point in time and then execute a second algorithm that determines an optimal dose of insulin for a later point in time. For example, the different or changing pharmacokinetic profile can be determined by detecting a change in a patient's glycemic pattern, announcement or products codes entered by the user via the UI 20, signaling from the insulin reservoir via radio-frequency identification (RFID) or the like, reading bar codes (e.g., printed on components of an insulin set), etc. In response to determining a different or changing pharmacokinetic profile via glycemic patterns, the system 10, via the controller 24, can execute an algorithm that uses an updated set of parameter values to determine an optimal insulin dose that accommodates for the current pharmacokinetic profile. Various examples of accommodating for varying pharmacokinetic profiles are discussed herein.

In certain embodiments, the MMPC algorithm 100 can be adapted to accommodate for the above-described differing and/or changing (e.g., progressive) pharmacokinetic profiles. The controller 24 can determine that a pharmacokinetic profile has changed (e.g., progressed over time) and/or is otherwise different and, in response, execute the MMPC algorithm 100 to accommodate for the determined pharmacokinetic profile. As noted above, the controller 24, via the MMPC algorithm 100, computes a plurality of state models at certain time intervals and uses one or more of the computed state-models to determine an optimal insulin dose at a given point in time. The state models are computed based a variety of model parameters and their values that affect how each model determines an insulin dose. In certain embodiments, upon determining differing and/or changing pharmacokinetic profiles, the controller 24 will compute the state models more or less often (e.g., execute the MMPC algorithm 100 more or less often). In certain embodiments, upon determining differing and/or changing pharmacokinetic profiles, the controller 24 will compute the state models by applying a new set of model parameters and/or a new set of values of the model parameters.

In certain embodiments, to determine differing and/or changing pharmacokinetic profiles, the controller 24 monitors trends in a patient's glucose levels (e.g., glycemic patterns). For example, the controller 24 monitors the physiological glucose concentration values provided by the CGM 22 and compares the physiological glucose concentration values to a database (e.g., table) of physiological glucose concentration values and associated insulin pharmacokinetics (e.g., insulin pharmacokinetics values and/or profiles). The database of physiological glucose concentration values can include expected or past physiological glucose concentration values, rates, and/or time periods for a given amount of delivered insulin. In another example, the controller 24 monitors the physiological glucose concentration values provided by the CGM 22 and compares the physiological glucose concentration values to those physiological glucose concentration values and associated insulin pharmacokinetics (e.g., insulin pharmacokinetics values and/or profiles) determined by a learning algorithm adapted to a patient's individual metabolic patterns. For example, the learning algorithm may include data processing and analysis that determines, over time, how an individual patient reacts to insulin.

In certain embodiments, the controller 24 determines patients' glycemic patterns by utilizing known insulin-to-carbohydrate ratios. For example, the controller 24 via the UI 20 may request that a patient, after fasting, consume a standardized meal (which could comprise a small meal such as a snack) such as a glucose tablet, a piece of candy, or other food with a known quantity of macronutrient content (e.g., known quantity of simple carbohydrates). Along with the standardized meal, the controller 24 causes delivery of a pre-determined insulin bolus based on the amount of carbohydrates consumed with the standardized meal (e.g., a known insulin-to-carbohydrate ratio). The controller 24, via the MMPC algorithm 100, could then analyze glycemic patterns of the patient's response to the meal and insulin bolus. In certain embodiments, analyzing glycemic patterns involves determining at least one of the glucose $t_{max}$ (e.g., the elapsed time from carbohydrate ingestion and insulin dosing to a maximum reduction in glucose levels), early 50% $t_{max}$ (e.g., the elapsed time from carbohydrate ingestion and insulin dosing to the half-way point leading up to the maximum reduction in glucose levels), late 50% $t_{max}$ (e.g., the elapsed time from carbohydrate ingestion and insulin dosing to the half-way point back to baseline following a maximum reduction in glucose levels) and an area under the glucose curve (AUC) over a predetermined period of time and comparing the value(s) against a lookup table. In other embodiments, the patient may announce via the UI 20, after fasting overnight, a standardized breakfast for which the carbohydrate content is accurately known rather than ingesting a glucose tablet, piece of candy, etc., outside of mealtimes.

In addition to determining patients' glycemic patterns, the controller 24 can determine a type of insulin being used and adjusts insulin delivery (e.g., basal rate) accordingly. For example, the controller 24, upon determining that a new infusion site is being used (e.g., by detecting change in pump cartridge, by detecting a pump priming command), analyzes a patient's glycemic patterns to determine a type of insulin being used or that a different insulin is being used. Such a determination may involve comparing a current or expected incremental AUC following insulin bolus dosing with the known incremental AUC over a set period of time. For example, in the first hour after insulin delivery on days 0-1 of an infusion set, an expected incremental glucose AUC for ultra-rapid insulin is approximately 20-45% lower than that of a traditional fast-acting insulin.

In some embodiments, if the monitored physiological glucose concentration values are different than the compared values in the database, this may indicate that a patient is processing a certain insulin differently than expected which may indicate loss of infusion site efficacy. In certain embodiments, differing and/or changing pharmacokinetic profiles are monitored and identified in real time or in near-real time.

In certain embodiments, upon determining differing and/or changing pharmacokinetic profiles, the controller 24 will compute the state models more or less often. As mentioned above, the controller 24 receives glucose data (including a patient's glucose concentration) from the CGM 22 at predefined intervals (e.g., every 5 or 10 minutes). With slower-acting insulins, there may be little to no benefit of computing the state models at each predefined interval. However, because faster-acting insulins take effect more quickly (i.e., changes in blood glucose occur more quickly), upon detecting use of a faster-acting insulin, the controller 24 may collect the glucose data and/or compute the state models more often (e.g., every 5 minutes rather than every 10 minutes) to maintain tighter glycemic control. Conversely, because slower-acting insulins take effect less quickly, upon detecting use of a slower-acting insulin, the controller 24 may collect the glucose data and/or compute the state models less often (e.g., every 10 minutes rather than every 5 minutes).

In certain embodiments, the controller 24 will collect the glucose data and/or compute the state models more or less often (e.g., execute the MMPC algorithm 100 more or less often) based on a resting state of the patient-regardless of the type of insulin being used by the patient. For example, the controller 24 may collect the glucose data and/or compute the state models more or less often depending on whether the patient is awake, asleep, nearly asleep, and/or nearly awake. When a patient is asleep, changes in the patient's glucose occur more slowly because, for example, no meals are consumed and because the patient is not exercising. As such, in certain embodiments, the controller 24 is programmed to collect the glucose data and/or compute the state models less often when the patient is asleep. For example, the controller 24 may be programmed to collect the glucose data and/or compute the state models less often at predetermined certain times of the day (e.g., 10 PM to 6 AM) when a patient is asleep. For example, during the hours of 6 AM and 10 PM, the controller 24 will compute the state models every five minutes, but during the hours of 10 PM and 6 AM, the controller 24 will compute the state models every ten minutes. Computing the state models less often saves battery power. In certain embodiments, the particular times of the day to trigger a change in computing and/or collecting intervals can be modified by the patient via the UI 20. In certain embodiments, the controller 24 is configured to detect the onset of sleep, becoming awakened, and/or patient-specific trends in response to meal patterns (e.g., determining a patient's typical eating pattern), lulls in glucose excursions, accelerometer data from wearables, frequency of the user's access to the UI 20, and the like. Upon such detection, the controller 24 can change the timing of collection of glucose data and/or computation of the state models. In addition to, or independently from, computing the state models more or less often based on a resting state of the patient, the controller 24 may reduce the period of time between microbolus and/or basal delivery. For example, the controller 24 may issue a command to the pump 12 to carry out fewer pump strokes in a given period of time (e.g., from one pump stroke every 5 or 10 minutes to every 15 minutes). Reducing the number of pump strokes can reduce power consumption.

In certain embodiments, upon determining differing and/or changing pharmacokinetic profiles, the controller 24 will compute the state models with a different set of model parameters to accommodate for the determined pharmacokinetic profiles. As noted above, to compute the state models, the MMPC algorithm 100 uses model parameters such as insulin sensitivity ($S_I$), insulin time constant ($k_I$), the meal action time constant ($k_C$), sensor time constant ($k_{SENSOR}$), insulin-to-carbohydrate ratio (ICR), input values at the UI 20, preprogrammed/stored values in the memory readable by the controller 24, and/or a combination of these options. One or more of these model parameters' values can be changed such that the state models are computed using an updated set of model parameter values. Below in the following paragraphs are examples of how the controller 24 may compute the state models with a different set of model parameter values upon determining differing and/or changing pharmacokinetic profiles. These examples are also applicable for situations when the controller 24 determines differing and/or changing pharmacokinetic profiles in response to receiving input (e.g., via the UI 20 and the like) that a different insulin is or will be used by the patient. In certain embodiments, upon determining differing and/or changing pharmacokinetic profiles, the predetermined physiological glucose concentration is reduced (e.g., from 6 mmol/L to 5 mmol/L).

In one example, the controller 24 changes the models parameter values that affect how the MMPC algorithm 100 addresses meal announcements. As described above, when a meal is announced (e.g., via the UI 20), the physiological glucose target ($PG_{TGT}$) is raised by 0.9-1.4 mmol/L and then gradually lowered back to its starting point via a linear decay profile over the course of a predetermined time period (e.g., 210 minutes) following the meal announcement. With a faster-acting insulin, the aggressiveness of meal bolus dosing can be increased. An increase in aggressiveness may take many forms, including an increase in the insulin-to-carbohydrate ratio (ICR), an increase in basal rate, a decrease in the predetermined time period (e.g., from 210 minutes to 80-120 minutes) following the meal announcement, a decrease in the magnitude (or weighting) of the effect of the cost functions described above by 10-30% (e.g., an increase in the decay of the effect of a meal), a 10-20% increase in the model parameter $S_P$ which is a scaling factor that controls in part, at least, the effect of insulin on physiological glucose, and/or increasing a gain value (e.g., overall gain value) of the controller 24.

In another example, the controller 24 changes the values of the model parameters that affect how the MMPC algorithm 100 addresses errors in estimating physiological insulin levels, which may not be directly measured and/or collected. The errors in estimating physiological insulin levels are accounted for by the MMPC algorithm 100 via the insulin compartments of the covariance matrices of the state models. When a faster-acting insulin is used, estimating physiological insulin levels tends to become more accurate. As such, the insulin compartments may be adjusted, for example, by reducing the insulin compartments by 10-30% compared with the default insulin compartments.

In another example, the controller 24 changes the values of the model parameter that affect how the MMPC algorithm 100 addresses what is sometimes referred to as the "dawn phenomenon." The dawn phenomenon occurs somewhat unpredictably for many patients and involves situations in which a patient's blood glucose rises in the early morning hours. This decreases insulin sensitivity and potentially leads to difficult-to-correct hyperglycemia. With a slower-acting or a faster-acting insulin, the basal rate can be increased to more aggressively control the target glucose level in response to detecting the dawn phenomenon or that the dawn phenomenon is about to occur. The controller 24 can make such a detection by, for example, analyzing and identifying glycemic pattern or patterns involving an upward trend in a patient's glucose values 1-3 hours before the patient wakes. In response, the controller 24 can increase the basal rate at a first predetermined period of time (e.g., 1.5-2 hours) in advance of the predicted onset, if a slower-acting insulin is being used, or at a second, shorter predetermined period of time (e.g., 1-1.5 hours) if faster-acting insulin is being used. In certain embodiments, upon detecting the dawn phenomenon, the controller 24 computes fewer models by not computing models that would have otherwise utilized one or more of the higher values of insulin sensitivity ($S_I$). After a certain period of time (e.g., after pre-dawn hours), the controller 24 may revert back to computing models with all of the stored values for insulin sensitivity.

In another example, the controller 24 changes the values of model parameters that affect how the MMPC algorithm 100 addresses an announcement of exercise. As described above, when exercise is announced (e.g., via the UI 20), the physiological glucose target ($PG_{TGT}$) is raised by 3 mmol/L. Because a faster-acting insulin will enable more rapid response of the algorithm to changes in glucose levels, the physiological glucose target ($PG_{TGT}$) could be raised by just 2 mmol/L-resulting in a more rapid glycemic recovery after exercise. In certain embodiments, if exercise was announced during the previous day, the controller 24 computes fewer models during pre-dawn hours by not computing models that would have otherwise utilized one or more of the lower values of insulin sensitivity ($S_I$). However, upon detecting the dawn phenomenon, the controller 24 may revert back to computing models with all of the stored values for insulin sensitivity.

In another example, the controller 24 changes the values of the model parameters that affect how and when the MMPC algorithm 100 changes a basal pattern, including the basal rate. For example, the basal pattern can be changed in response to the dawn phenomenon (as described above), site efficacy issues including the Tamborlane Effect (described above), or changes in post-prandial glucose patterns, and/or mean daily glucose levels. When the basal pattern changes, the controller 24 may change the model parameter values that affect how the MMPC algorithm 100 limits how much and the rate at which the basal pattern changes. For example, the MMPC algorithm 100 may include a series of safety checks that limit the aggressiveness of the basal pattern and any changes of the basal pattern to reduce the risk of hypoglycemia to the patient. In some embodiments, the MMPC algorithm 100 does not include limits to the amount by which the basal rate may be increased or decreased. For example, for days 1-3 of an infusion set, the MMPC algorithm 100 may remove upper basal rate limits, and beyond day 3, increase upper basal rate limits. In certain embodiments, when a limit has been reached, an alert or alarm for the patient is initiated via the UI 20. In certain embodiments, an alert or alarm is initiated upon changing the model parameter values to a more aggressive basal pattern or upon determining that a pharmacokinetic profile is changing (e.g., a loss of infusion site efficacy). For example, the alert or alarm could signal to the patient that the infusion set 18 associated with the system 10 should be changed. In some embodiments, a patient using an ultra-rapid insulin may expect that ~58% more insulin will be transported to the blood stream within 15 minutes of dosing on days two to three compared with days zero to one, whereas a patient using traditional fast-acting insulins such as Humalog will experience only a ~38% difference between day three and day one. As site efficacy changes on days two to three, the controller 24 may then adjust basal and bolus timing and patterns to accommodate for the expected ~58% increase within the first 15 minutes of an insulin dose. In addition, as a single infusion site is maintained, the controller 24 may become more aggressive if a patient is using ultra-rapid insulin compared to traditional rapid-acting insulin by delivering larger boluses during hyperglycemia, delaying suspension (discussed below) of insulin on trending hypoglycemia, earlier resumption of insulin delivery following a suspension (discussed below), and the like.

In embodiments, as a single infusion site in maintained, the controller 24 detects a loss of infusion site efficacy due to a patient processing a certain insulin differently over time. For example, the controller 24 monitors trends in basal or microbolus clustering, magnitude, and/or total daily dose and accommodates the loss in efficacy by delivering more basal insulin. Accommodating for the loss in efficacy may enable patients to use an infusion set for longer (e.g., an extra 24 hours) than the typical 2-3 days. However, in some embodiments, the controller 24 limits the increase in basal delivery or total daily dose compared with that from days 0-1, and upon reaching the limit, the controller 24 via the UI 20 may indicate to the patient that the infusion set needs to be changed.

In another example, the controller 24 limits the number of state models computed by the MMPC algorithm 100 by limiting the number of model parameter values used by the MMPC algorithm 100. For example, when a faster-acting insulin is being used by a patient, the MMPC algorithm 100 may not need to compute models involving model parameters associated with long insulin action times (e.g., insulin time constant ($k_I$)) and meal action times (e.g., meal action time constant ($k_C$)). With a faster-acting insulin, the long action times may not be reasonable approximations of a patient's metabolism and therefore unlikely to be helpful for determining an optimal insulin dose by the MMPC algorithm 100. Reducing the number of models computed by the controller 24 may reduce battery power and/or how much memory the system 10 uses. In certain embodiments, the controller 24 changes the model parameter values to reduce the range of insulin action times in $\tau_{isub}$, for example by reducing the range from 57-78 minutes to 47-68 minutes to further improve glycemic control.

In another example, the controller 24 changes the values of the model parameters that affect how the MMPC algorithm 100 addresses mealtime bolusing. As described above, mealtime bolus calculators used in both open and closed loop systems can be tuned to assist in correcting meals by attenuating the Insulin On-Board (IOB) parameter and/or the insulin-to-carbohydrate ratio (ICR), which are used in calculating boluses. For example, the IOB and/or ICR used on day three of use of a single infusion site may be attenuated compared with the IOB and/or ICR used on day zero. Such an adaptive bolus calculator may be used in concert with an adaptive basal pattern that increases aggressiveness over time as changes in insulin pharmacokinetics are detected.

In another example, the controller 24 changes the values of the models parameter that affect how the MMPC algorithm 100 suspends insulin delivery. The MMPC algorithm 100 may be programmed to suspend insulin delivery based on a physiological glucose concentration and/or rate and direction of change of the physiological glucose concentration. In certain situations, suspending insulin delivery reduces the risk of hypoglycemia. Guidelines (e.g., rule sets) for suspending insulin delivery can vary depending on certain conditions. For example, for a given range of physiological glucose concentration values estimated by the MMPC algorithm 100, the MMPC algorithm 100 may be programmed to suspend insulin delivery if a change in estimated physiological glucose concentration exceeds an associated threshold. The MMPC algorithm 100 may follow one set of guidelines for different conditions. For example, the MMPC algorithm 100 may follow one set of guidelines (e.g., rule sets each with ranges of physiological glucose concentration values and associated thresholds) when no meal or exercise has been announced, another set of guidelines for conditions when a meal or exercise has been announced, and an overall set of guidelines to be applied regardless of whether a meal or exercise has been announced. In certain embodiments, upon determining differing and/or changing pharmacokinetic profiles the controller 24 utilizes fewer rule sets within each of the various sets of guidelines when determining whether to suspend and/or resume insulin delivery. For example, if a set of guidelines included five rule sets (e.g., five ranges of physiological glucose concentration values and associated thresholds for suspension and/or resumption), the controller 24 could utilize only three of the five rule sets in determining whether to suspend and/or resume insulin delivery. The unutilized rule sets could be the more conservative rule sets (e.g., rule sets with comparatively higher ranges of physiological glucose concentration values and associated thresholds for suspension and/or resumption).

After basal insulin delivery is suspended or attenuated, the system 10 will resume normal basal insulin delivery once criteria in the guidelines no longer apply or after a maximum period of time (e.g., two hours), whichever occurs first. In certain embodiments, if basal insulin delivery is suspended for two or more hours, the system 10 automatically reverts to an open loop mode, and the patient must reinitialize the system 10 to resume closed loop therapy. A risk with prolonged insulin suspension is hyperglycemia associated with loss in regulation of hepatic glucose production, which can be difficult to correct in a timely manner once basal insulin delivery is resumed and which can lead to diabetic ketoacidosis (DKA). With faster-acting insulins, correction of physiological glucose concentration occurs more quickly, which reduces risks for hyperglycemia and DKA. Further, with faster-acting insulins, the guidelines for suspending and resuming basal insulin delivery can be adjusted to delay suspension and resume more quickly, thus providing tighter glycemic control and reduced risk of hypoglycemia or hyperglycemia. For example, in the absence of an announced meal or exercise, the thresholds for physiological glucose concentration levels may be lowered and/or the rates of change needed to trigger suspension may be increased. This would delay suspension and would also trigger an earlier resumption once the criteria in the guidelines are no longer met. In another example, with announcement of meal or exercise, the threshold physiological glucose concentration levels may be lowered and/or the rates of change needed to trigger suspension may be increased, and/or the rates of change needed to trigger resumption may be decreased. This would in turn delay suspension and trigger an earlier resumption once these criteria are no longer met. In another example, under any condition, the physiological glucose concentration thresholds to suspend may be slightly lower. In another example, the maximum period of time allowed for suspension can be reduced (e.g., ninety minutes), resulting in reducing the risk for post-suspension rebound hyperglycemia caused by an increase in hepatic glucose production that would otherwise be inhibited by insulin delivery.

In certain embodiments, the controller 24 calculates and provides bolus recommendations to the patient via the UI 20. Bolus recommendations can be dependent on factors such as the amount of carbohydrates, fat, and/or protein in a meal, and/or the duration of infusion set wear. The bolus recommendations can be in a multi-wave pattern where in a first bolus wave, immediately following meal announcement, the bolus recommendations are a fraction of the predicted bolus need. For example, during days 0-1, a recommended multi-wave bolus in response to a large or complex meal, may comprise a first wave of greater than 50% (e.g., 60-80%) of the bolus immediately on announcement of a meal, and the remaining fraction of the bolus being delivered over a period of time (e.g., 3 hours) following the meal announcement. On day two and later, the recommended multi-wave bolus can be split among first wave of ~50% of the bolus with the remaining ~50% of the bolus being delivered over the period of time following the meal announcement. In certain embodiments, at least part of the multi-wave bolus resembles a square wave. In certain embodiments, before the second bolus wave, the controller 24 via the UI 20 can receive an updated meal announcement to change the amount of bolus given in the second bolus wave. This permits a patient to update a meal announcement should they consume more or less than originally predicted-thus reducing the risk of over-predicting and over-bolusing, which potentially leads to hypoglycemia. With a faster-acting insulin, the timing of meal announcements (and therefore mealtime boluses) is less critical than with slower-acting insulins. As such, the bolus recommendations can be provided to the patient anywhere from ten minutes before to ten minutes after beginning a meal. For slower-acting insulin, the timing for bolus recommendations can be similar to the bolus recommendations for faster-acting insulins once the Tamborlane Effect has been detected or is predicted to have begun.

Figure 11:
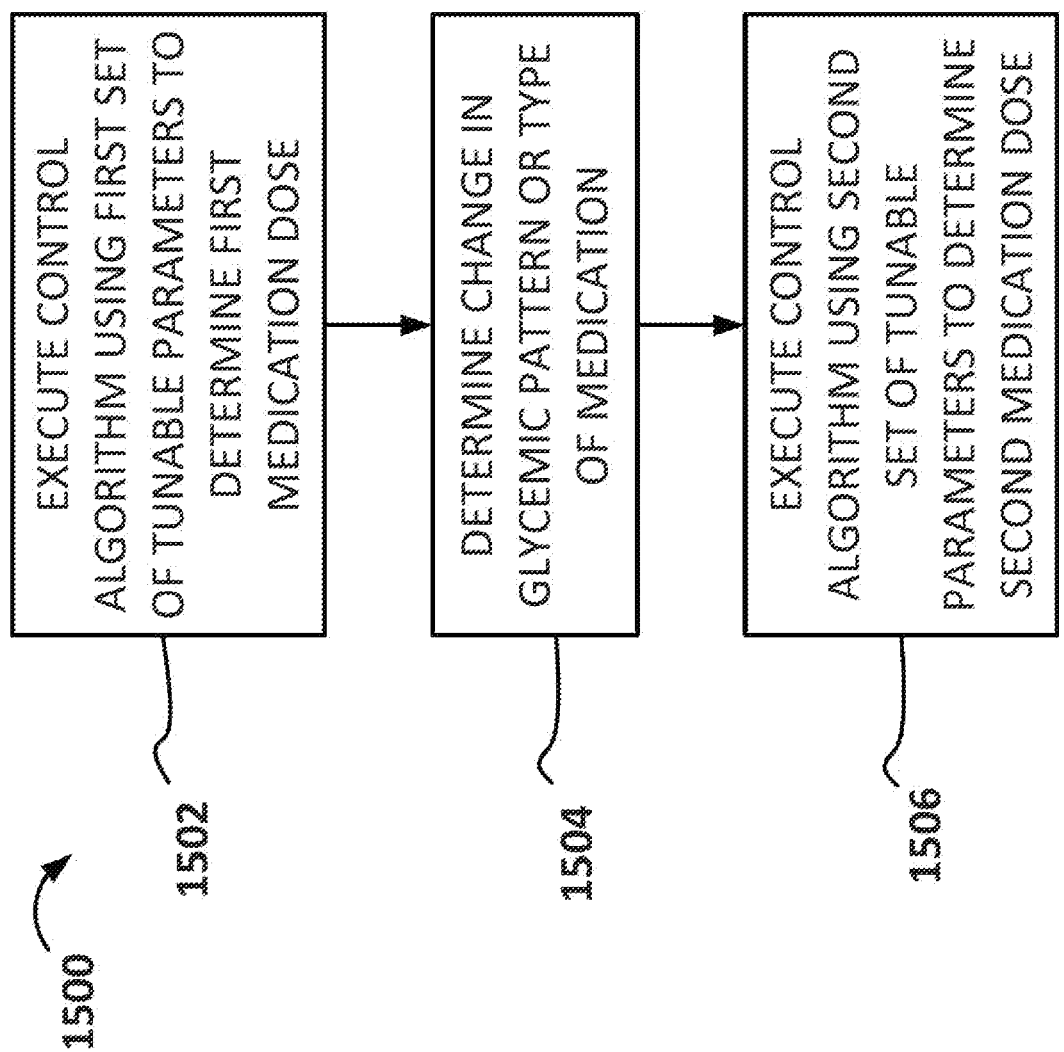
FIG. 11 depicts a flowchart detailing various example logic, which may be applied when determining an amount of drug (e.g., insulin) to be delivered.

Various alternatives and modifications may be devised by those skilled in the art without departing from the present disclosure. In particular, although the disclosure uses a model-based controller to ultimately determine and deliver an appropriate amount of insulin to a patient, features of the disclosure can apply to other types of control algorithms (e.g., proportional-integral-derivative (PID) control algorithm, a fuzzy logic control algorithm, and the like). FIG. 11 shows an example method 1500 with steps that could be carried out by the system 10 using various control algorithms. The method 1500 includes executing a control algorithm, using a first set of tunable parameters, to determine a first medication dose (step 1502). Upon determining a change in a glycemic pattern and/or a type of medication (step 1504), the method 1500 includes executing the control algorithm, using a second set of tunable parameters, to determine a second medication dose (step 1506). Like model-based control algorithms, a PID control algorithm may use tunable parameters to compute insulin delivery amounts. Using a PID control algorithm as an example, the tunable parameters may include insulin-on-board (e.g., the proportional in PID), a difference between a measured glucose level and a target glucose level (e.g., the integral in PID), and a rate of change of glucose (e.g., the derivative in PID). Those tunable parameters may be changed in response to determining a change in a glycemic pattern and/or a type of medication. For example, the insulin-on-board may be increased or decreased in response to detecting such a change. As such, after the detected change, the PID control algorithm will ultimately compute insulin delivery amounts using the increased or decreased insulin-on-board.

Accordingly, the present disclosure is intended to embrace all such alternatives, modifications and variances. Additionally, while several embodiments of the present disclosure have been illustrated in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A system for providing closed-loop control of physiological glucose, comprising:
    a drug delivery device configured to receive a first drug reservoir containing insulin and a second drug reservoir containing glucagon;
    a user interface configured to receive user input comprising exercise data;
    a glucose measuring device configured to measure a current interstitial glucose; and
    a controller,
    wherein in response to receipt of the exercise data, the controller is configured to estimate a physiological glucose based on the measured current interstitial glucose, calculate a corrected physiological glucose by subtracting an exercise factor from the estimated physiological glucose, and based on the calculation, to cause a glucagon bolus and an insulin bolus to be delivered in a closed-loop,
    wherein the glucagon bolus is deliverable only when a rate of change of the physiological glucose is less than a glucose rate threshold, and
    wherein the glucose rate threshold is a function of the estimated physiological glucose.

2. The system according to claim 1, wherein the glucose rate threshold is less than zero for the glucagon bolus to be delivered.

3. The system according to claim 1, wherein a glucagon bolus volume or size scales with the rate of change of physiological glucose and the estimated physiological glucose.

4. The system according to claim 2, wherein the glucagon bolus increases with decreasing rate of change of physiological glucose and/or decreasing estimated physiological glucose.

5. The system according to claim 1, wherein the rate of change of physiological glucose is calculated as a difference between two successive estimated physiological glucose values if the estimated values are based on measurements of the current interstitial glucose at fixed intervals.

6. The system according to claim 1, wherein doses of glucagon are set to zero or canceled for a period after a meal.

7. The system according to claim 6, wherein the doses of glucagon are set to zero or canceled for 2 hours after the meal.

8. The system according to claim 1, wherein the exercise factor is 3 mmol/L.

9. A system for providing closed-loop control of physiological glucose, comprising:
    a drug delivery device configured to receive a first drug reservoir containing insulin and a second drug reservoir containing glucagon;
    a user interface configured to receive user input comprising exercise data;
    a glucose measuring device configured to measure a current interstitial glucose; and
    a controller,
    wherein in response to receipt of the exercise data, the controller is configured to estimate a physiological glucose based on the measured current interstitial glucose, calculate a corrected physiological glucose by subtracting an exercise factor from the estimated physiological glucose, and based on the calculation, to cause increased doses of the glucagon and doses of the insulin to be delivered in a closed-loop.

10. The system according to claim 9, wherein the doses of glucagon are set to zero or canceled for a period after a meal.

11. The system according to claim 10, wherein the doses of glucagon are set to zero or canceled for 2 hours after the meal.

12. The system according to claim 9, wherein the exercise factor is 3 mmol/L.

* * * * *